United States Patent
Yamamoto et al.

(10) Patent No.: US 8,324,427 B2
(45) Date of Patent: Dec. 4, 2012

(54) SUBSTANCES ANALOGOUS TO MK8383 AND AGRICULTURAL AND HORTICULTURAL DISEASE CONTROL AGENTS

(75) Inventors: Kentaro Yamamoto, Kawasaki (JP);
Nobuto Minowa, Yokohama (JP);
Masahisa Nakada, Tokyo-To (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 285 days.

(21) Appl. No.: 12/921,947

(22) PCT Filed: Mar. 11, 2009

(86) PCT No.: PCT/JP2009/054686
§ 371 (c)(1),
(2), (4) Date: Sep. 10, 2010

(87) PCT Pub. No.: WO2009/113586
PCT Pub. Date: Sep. 17, 2009

(65) Prior Publication Data
US 2011/0065792 A1    Mar. 17, 2011

(30) Foreign Application Priority Data
Mar. 11, 2008   (JP) .................................. 2008-61652

(51) Int. Cl.
*C07C 61/29*   (2006.01)
*A01N 31/04*   (2006.01)
(52) U.S. Cl. ......................... 562/499; 562/501; 514/729
(58) Field of Classification Search .................. 562/499, 562/501; 514/729
See application file for complete search history.

(56) References Cited

U.S. PATENT DOCUMENTS
6,242,383 B1   6/2001   Wakui et al.

FOREIGN PATENT DOCUMENTS
JP   7-126211   5/1995
WO   99/11596   3/1999

OTHER PUBLICATIONS

Fujio et al.; JP 07-126211 A; 1995; Machine translation provided by PAJ on Jul. 30, 2012.*
Supplementary European Search Report dated Feb. 24, 2012 in Application No. EP 09719834.5.
International Search Report issued May 19, 2009 in International (PCT) Application No. PCT/JP2009/054686.
T. Suzuki et al., "First Total Synthesis of Antimitotic Compound, (+)-Phomopsidin", Organic Letters, vol. 6, No. 4, pp. 553-556, 2004.
M. Namikoshi et al., "Phomopsidin, A New Inhibitor of Microtubule Assembly Produced by *Phomopsis* sp. Isolated from Coral Reef in Pohnpei", The Journal of Antibiotics, vol. 50, pp. 890-892, Oct. 1997.
English translation of the International Preliminary Report on Patentability and Written Opinion dated Nov. 2, 2010.

* cited by examiner

*Primary Examiner* — Timothy Thomas
(74) *Attorney, Agent, or Firm* — Wenderoth, Lind & Ponack, L.L.P.

(57) ABSTRACT

An objective of the present invention is to provide agricultural and horticultural disease control agents that have potent control effect against plant diseases and, at the same time, have high photostability. The agricultural and horticultural disease control agents comprise a novel substance analogous to MK8383 as an active ingredient.

16 Claims, No Drawings

SUBSTANCES ANALOGOUS TO MK8383 AND AGRICULTURAL AND HORTICULTURAL DISEASE CONTROL AGENTS

This application is a U.S. national stage of International Application No. PCT/W2009/054686 filed Mar. 11, 2009.

FIELD OF INVENTION

The present invention relates to novel substances analogous to MK8383 and agricultural and horticultural disease control agents comprising the analogous substances as an active ingredient.

BACKGROUND ART

In the field of agriculture and horticulture, various fungicides are used for the control of plant diseases. The appearance of resistant strains and the like, however, has posed problems important to the control, for example, a problem of usage restrictions of existing agents.

MK8383 produced by microorganisms has a wide range of antimicrobial spectra against plant pathogenic filamentous fungi and is known as effective against a wide variety of plant diseases caused by filamentous fungi (Japanese Patent Application Laid-Open No. 126211/1995). On the other hand, MK8383 is known to be unstable against light. Accordingly, it has been desired that the development of agricultural and horticultural preparations having high disease control activity and high photostability.

Phomopsidin is known as a compound having a structure similar to the structure of MK8383 (J. Antibitics 1997, 50, 890-892), and the total synthesis of phomopsidin is also reported (Org. Letters 2004, 6, 553-556). However, it has not hitherto been reported any compound obtained by converting the double bond at the 1,2-positions of phomopsidin to a single bond.

SUMMARY OF THE INVENTION

The present inventor has found that novel compounds obtained by converting the double bound at the 1,2-positions of MK8383 to a single bond have a control effect, against plant pathogenic fungi, equivalent to MK8383 (Test Examples 1 and 3) and further have better photostability than MK8383 (Test Example 2). The present invention is based on the finding.

An objective of the present invention is to provide agricultural and horticultural disease control agents that have potent control effect against plant diseases and, at the same time, have high photostability.

According to the present invention, there are provided compounds represented by formula (I) or their agriculturally and horticulturally acceptable salts (hereinafter sometimes referred to as "compounds according to the present invention"):

[Chemical formula 1]

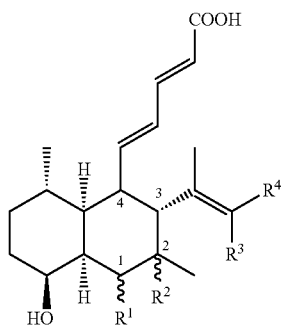

(I)

wherein
$R^1$ and $R^2$ represent a hydrogen atom, or $R^1$ and $R^2$ together combine with the carbon atom to which they are attached to form a cyclopropane ring, $R^3$ and $R^4$, which may be the same or different, represent a hydrogen atom or $C_{1-6}$ alkyl, and a wavy line represents that $R^1$, $R^2$, and methyl at the 2-position are independently in an alpha configuration or a beta configuration.

According to another aspect of the present invention, there are provided agricultural and horticultural disease control agents, comprising a compound according to the present invention as an active ingredient.

According to still another aspect of the present invention, there is provided a method for controlling plant pathogenic microorganisms, comprising applying an effective amount of a compound according to the present invention, to plant, seed, or soil.

According to a further aspect of the present invention, there is provided use of a compound according to the present invention, for the manufacture of an agricultural and horticultural disease control agent.

The compounds according to the present invention have a control effect, against plant pathogenic microorganisms, equivalent to MK8383 and further have better photostability than MK8383. Thus, they are useful as agricultural and horticultural disease control agents.

DETAILED DESCRIPTION OF THE INVENTION

Compounds According to Present Invention

In the specification of the present application, the term "alkyl" refers to straight chain or branched chain alkyl, and "$C_{1-6}$ alkyl" includes, for example, methyl, ethyl, n-propyl, iso-propyl, n-butyl, iso-butyl, sec-butyl, tert-butyl, n-pentyl, and n-hexyl.

In the specification of the present application, when the ring is placed on paper, if the substituent bonded to the ring faces the back of the paper, this substituent is expressed as an "alpha configuration" while, if the substituent bonded to the ring faces inward, this substituent is expressed as a "beta configuration."

In formula (I), preferably, $R^1$ and $R^2$ represent a hydrogen atom.

In formula (I), preferably, when one of $R^3$ and $R^4$ represents a hydrogen atom, the other represents $C_{1-6}$ alkyl.

Here $C_{1-6}$ alkyl preferably represents $C_{1-4}$ alkyl, more preferably $C_{1-2}$ alkyl, still more preferably methyl.

In formula (I), preferably, $R^1$ and $R^2$ are in an alpha configuration.

In formula (I), preferably, methyl at the 2-position is in a beta configuration.

In formula (I), more preferably, $R^1$ and $R^2$ are in an alpha configuration and methyl at the 2-position is in a beta configuration. Such compounds may be represented by the following chemical structural formula.

[Chemical formula 2]

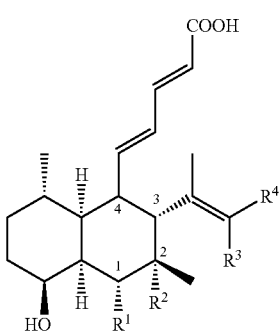

Compounds represented by formula (I) wherein $R^1$ and $R^2$ represent a hydrogen atom; and $R^3$ and $R^4$, which may be the same or different, represent a hydrogen atom or $C_{1-6}$ alkyl may be mentioned as a first group of compounds in the compounds according to the present invention.

Compounds represented by formula (I) wherein $R^1$ and $R^2$ represent a hydrogen atom; when one of $R^3$ and $R^4$ represents a hydrogen atom, the other represents $C_{1-4}$ alkyl; $R^1$ and $R^2$ are in an alpha configuration; and methyl at the 2-position is in a beta configuration may be mentioned as a preferred first group of compounds in the compounds according to the present invention. In a more preferred embodiment, compounds represented by formula (I) wherein $R^1$ and $R^2$ represent a hydrogen atom; when one of $R^3$ and $R^4$ represents a hydrogen atom, the other represents $C_{1-2}$ alkyl; $R^1$ and $R^2$ are in an alpha configuration; and methyl at the 2-position is in a beta configuration may be mentioned as the first group of compounds. In a further preferred embodiment, compounds represented by formula (I) wherein $R^1$ and $R^2$ represent a hydrogen atom; when one of $R^3$ and $R^4$ represents a hydrogen atom, the other represents methyl; $R^1$ and $R^2$ are in an alpha configuration; and methyl at the 2-position is in a beta configuration, ((2E,4E)-5-{(1S,4S,4aS,5S,6R,7S,8aR)-6-[(Z)-but-2-en-2-yl]-decahydro-1-hydroxy-4,7-dimethylnaphthalen-5-yl}penta-2,4-dienoic acid and (2E,4E)-5-{(1S,4S,4aS,5S,6R,7S,8aR)-6-[(E)-but-2-en-2-yl]-decahydro-1-hydroxy-4,7-dimethylnaphthalen-5-yl}penta-2,4-dienoic acid) may be mentioned as the first group of compounds.

In the present invention, the following compounds may be mentioned as examples of a suitable first group of compounds.

TABLE 1

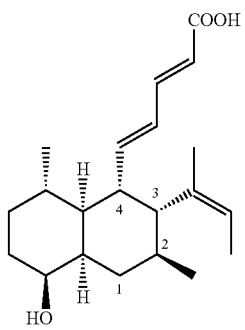

(Example 3)

TABLE 1-continued

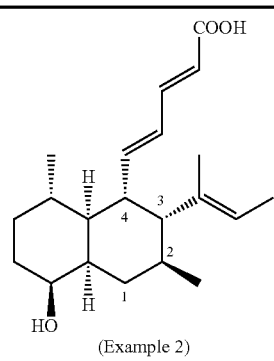

(Example 2)

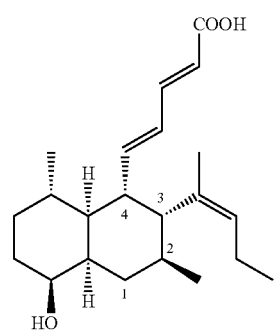

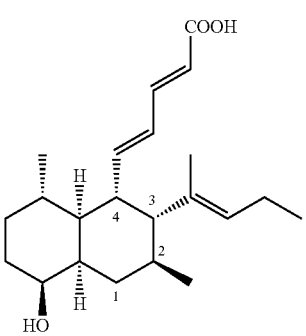

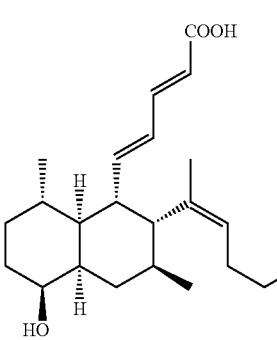

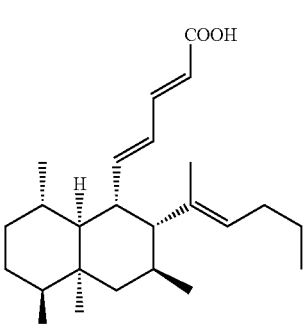

TABLE 1-continued
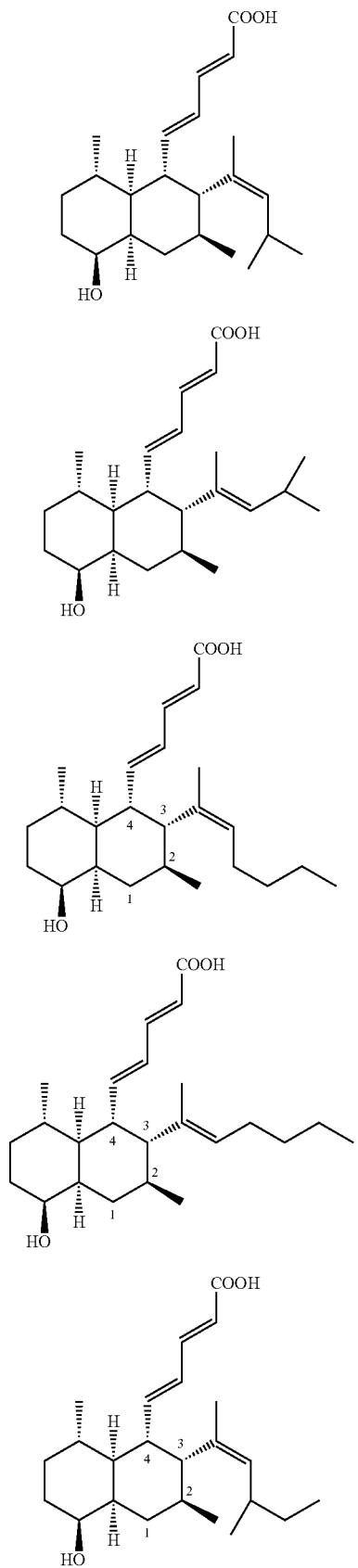
TABLE 1-continued
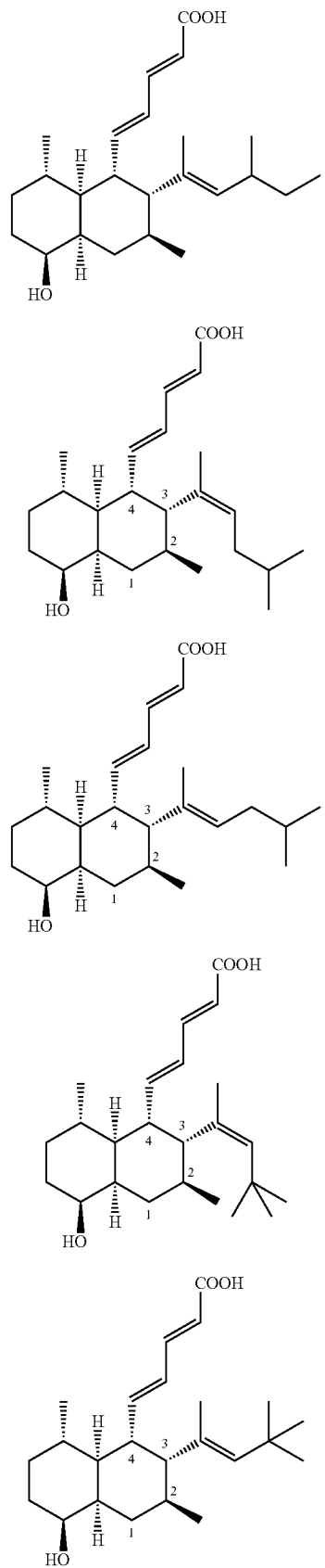

TABLE 1-continued
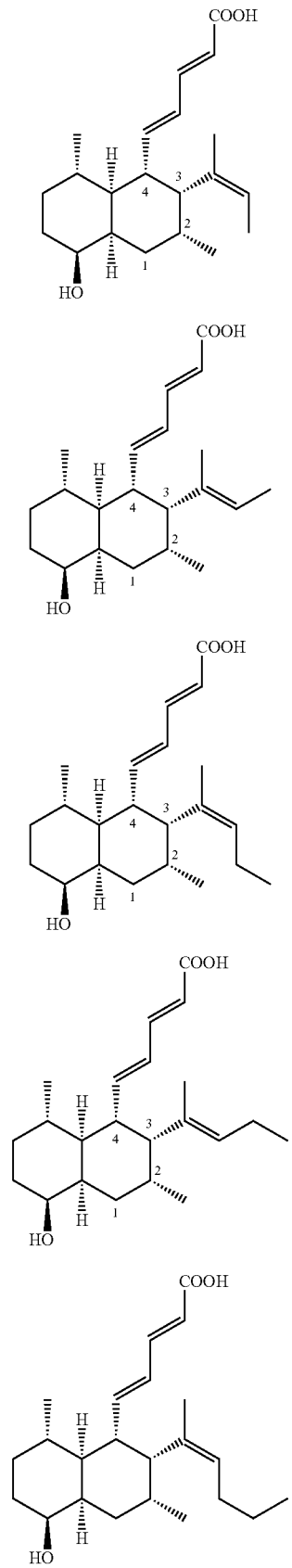
TABLE 1-continued
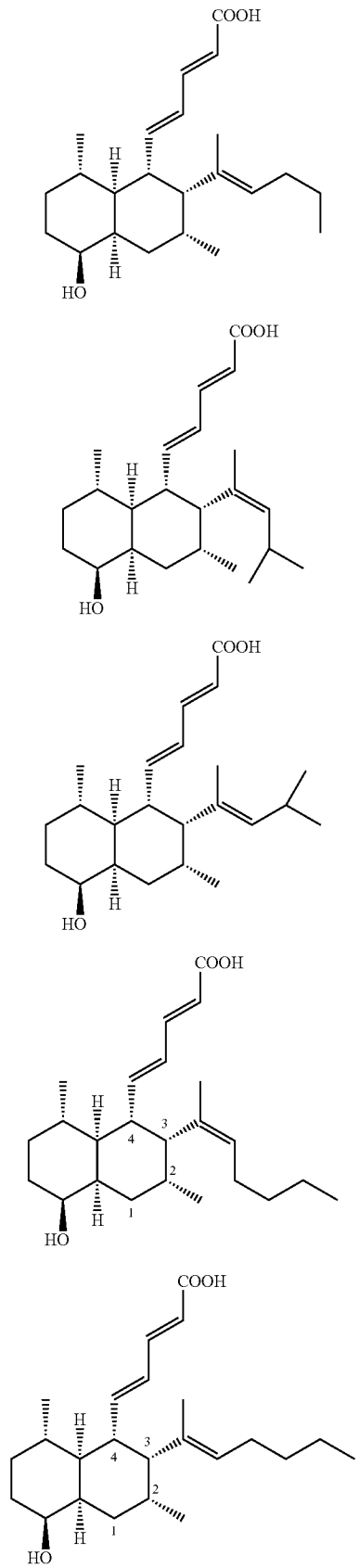

TABLE 1-continued

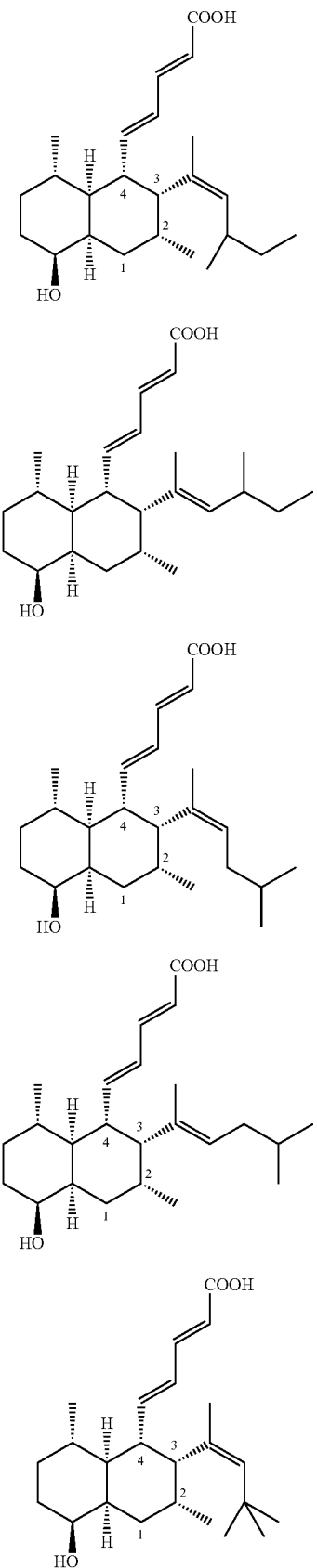

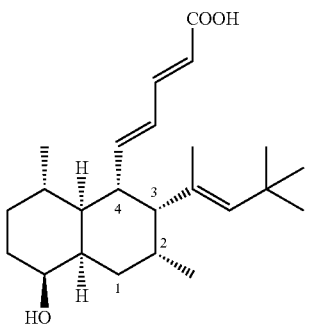

Compounds represented by formula (I) wherein $R^1$ and $R^2$ together combine with the carbon atom to which they are attached to form a cyclopropane ring; and $R^3$ and $R^4$, which may be the same or different, represent a hydrogen atom or $C_{1-6}$ alkyl may be mentioned as a second group of compounds in the compounds according to the present invention.

Compounds represented by formula (I) wherein $R^1$ and $R^2$ together combine with the carbon atom to which they are attached to form a cyclopropane ring; when one of $R^3$ and $R^4$ represents a hydrogen atom, the other represents $C_{1-4}$ alkyl; $R^1$ and $R^2$ are in an alpha configuration; and methyl at the 2-position is in a beta configuration may be mentioned as a preferred second group of compounds in the compounds according to the present invention. In a more preferred embodiment, compounds represented by formula (I) wherein $R^1$ and $R^2$ together combine with the carbon atom to which they are attached to form a cyclopropane ring; when one of $R^3$ and $R^4$ represents a hydrogen atom, the other represents $C_{1-2}$ alkyl; $R^1$ and $R^2$ are in an alpha configuration; and methyl at the 2-position is in a beta configuration may be mentioned as the second group of compounds. In a further preferred embodiment, compounds represented by formula (I) wherein $R^1$ and $R^2$ together combine with the carbon atom to which they are attached to form a cyclopropane ring; when one of $R^3$ and $R^4$ represents a hydrogen atom, the other represents methyl; $R^1$ and $R^2$ are in an alpha configuration; and methyl at the 2-position is in a beta configuration ((2E,4E)-5-{(1aR,2R,3S,3aS,4S,7S,7aS,7bR)-2-[(E)-but-2-en-2-yl]-decahydro-7-hydroxy-1a,4-dimethyl-1H-cyclopropa[a]naphthalen-3-yl}penta-2,4-dienoic acid) may be mentioned as the second group of compounds.

In the present invention, the following compounds may be mentioned as examples of a suitable second group of compounds.

TABLE 2

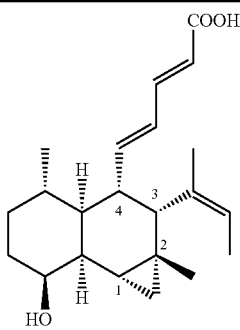

TABLE 2-continued
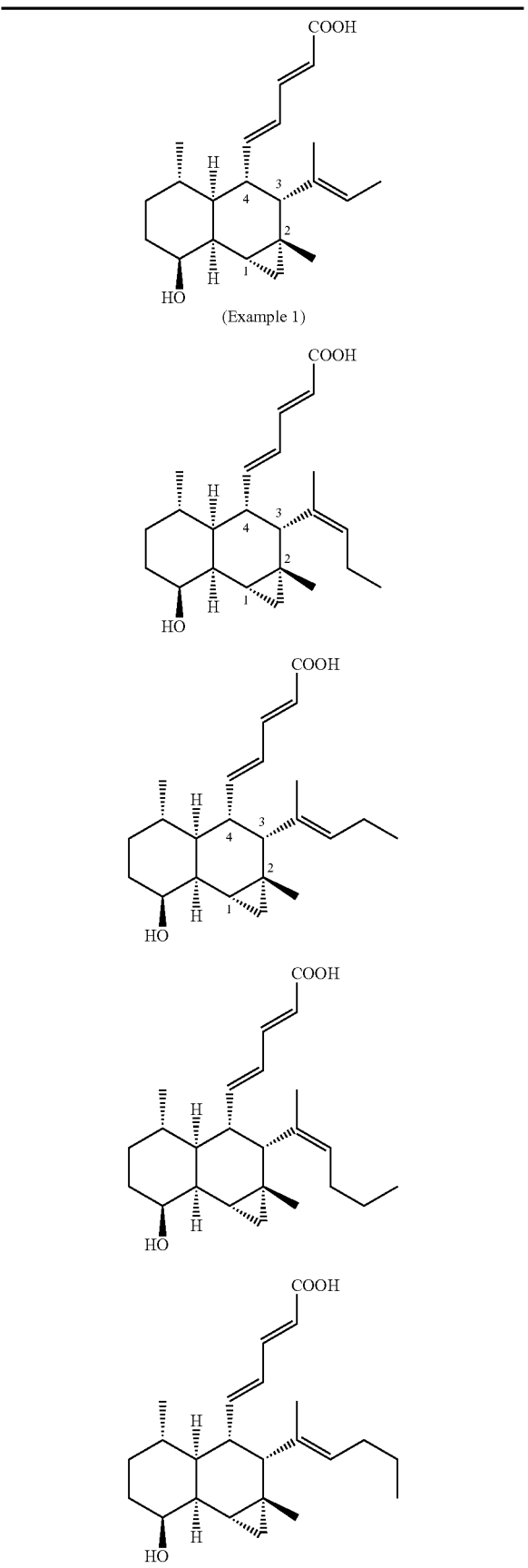
(Example 1)
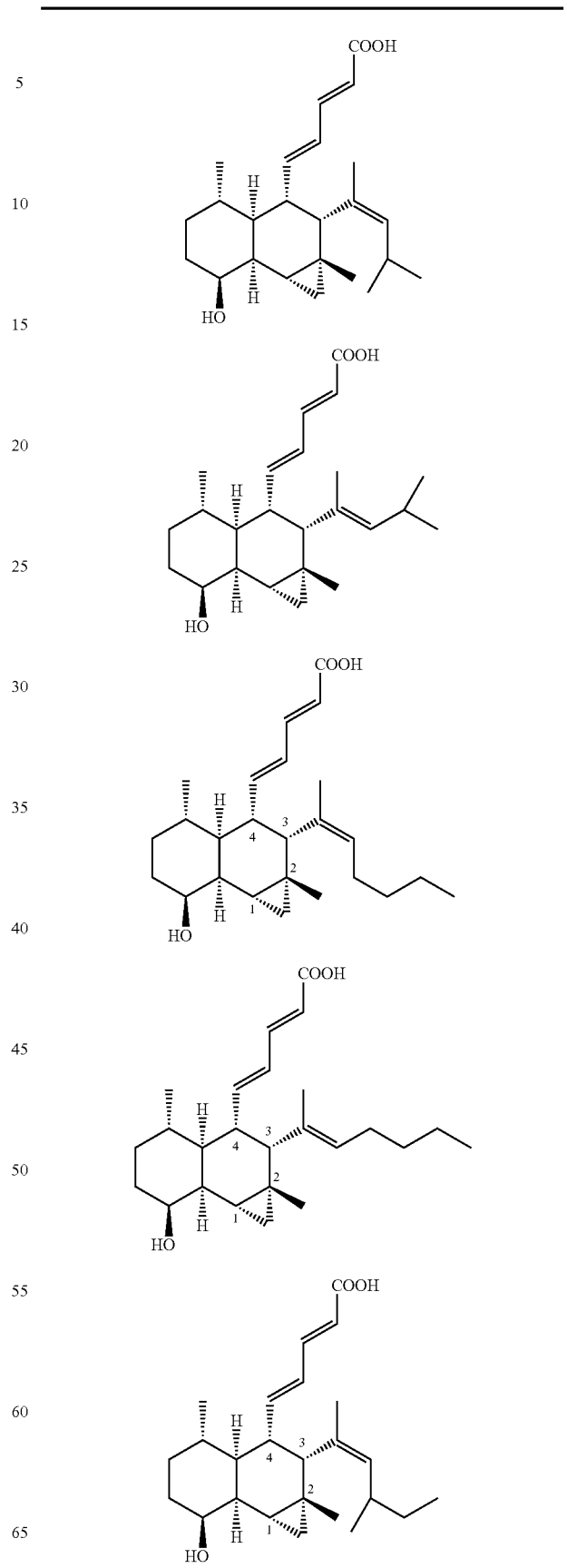

TABLE 2-continued

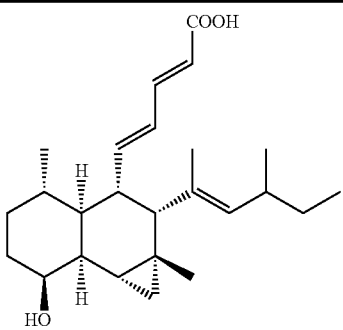

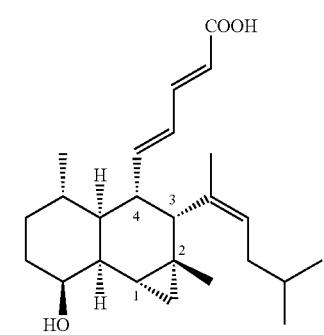

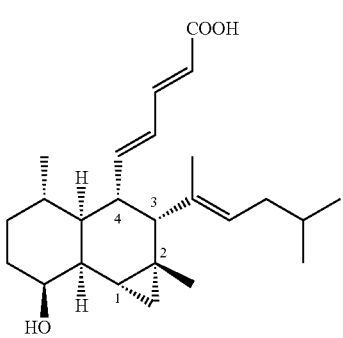

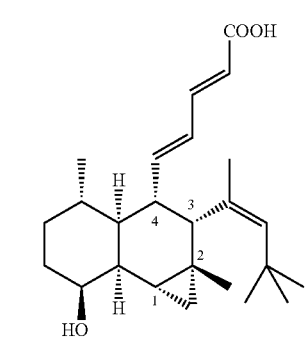

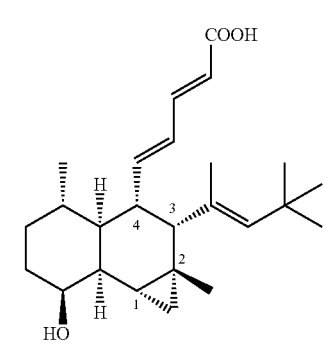

Agriculturally and horticulturally acceptable salts of compounds represented by formula (I) include, for example, alkali metal salts such as lithium salts, sodium salts, and potassium salts; alkaline earth metal salts such as magnesium salts and calcium salts; ammonium salts such as ammonium salts, methyl ammonium salts, dimethyl ammonium salts, trimethyl ammonium salts, and dicyclohexyl ammonium salts; organic amine salts such as triethylamine, trimethylamine, diethylamine, pyridine, ethanolamine, triethanolamine, dicyclohexylamine, procaine, benzylamine, N-methylpiperidine, N-methylmorpholine, and diethylanilne; and basic amino acid salts such as lysine, arginine, and histidine. Preferred are alkali metal salts, alkaline earth metal salts, and ammonium salts.

The compounds represented by formula (I) can be produced according to the following steps A to E.

Step A: Step of Cyclopropanation at 1,2-Positions

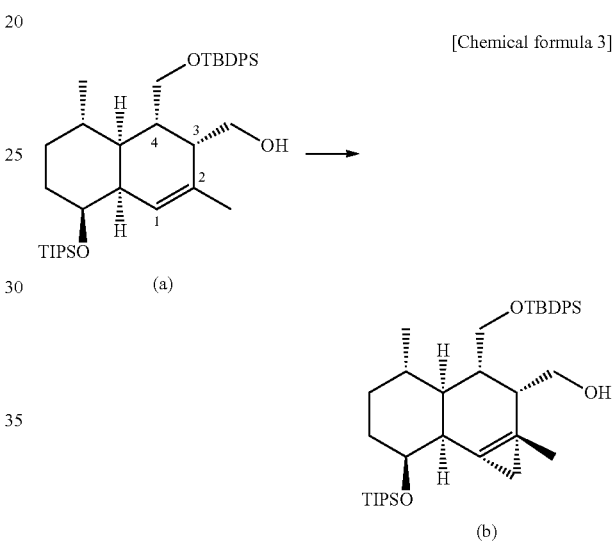

[Chemical formula 3]

In step A, the double bond at the 1-position of a compound of formula (a) is cyclopropanated to produce a compound of formula (b). The compound of formula (a) which is a starting compound can be synthesized by the method described in Org. Letters 2004, 6, 553-556. In the formula, TIPS represents triisopropylsilyl, and TBDPS represents tert-butyldiphenylsilyl.

Solvents usable in step A include chloroform, dichloromethane, and 1,2-dichloroethane. 1,2-Dichloroethane is preferred. Reactants usable in the cyclopropanation include diethyl zinc and diiodomethane. The reaction temperature may be 0° C. to 50° C. The reaction time may be 1 to 24 hr.

Step B: Step of Reduction at 1,2-Positions

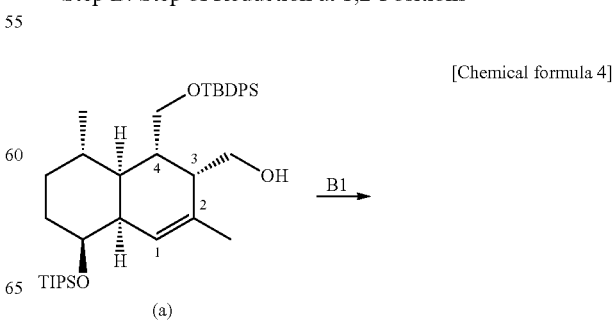

[Chemical formula 4]

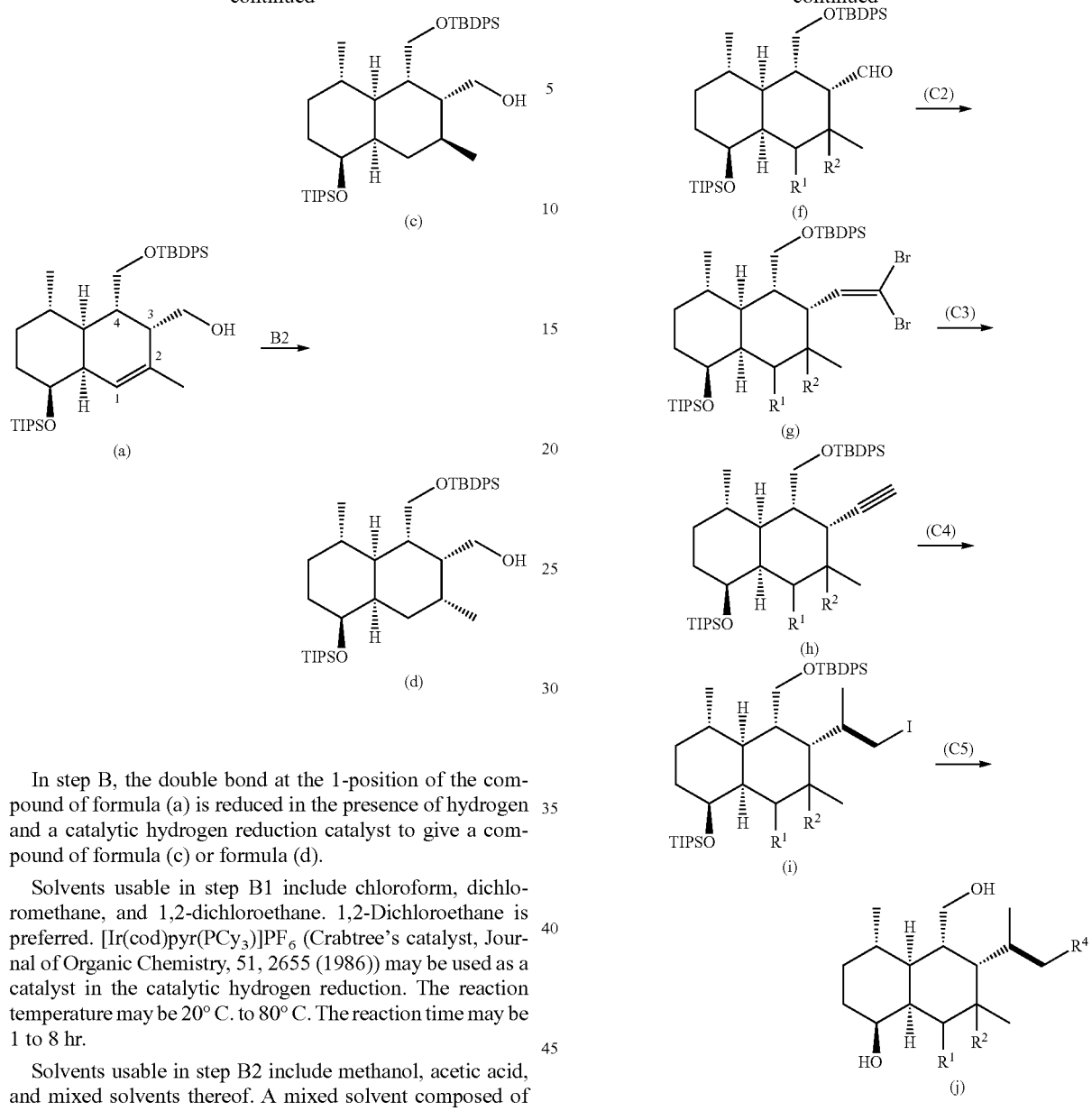

In step B, the double bond at the 1-position of the compound of formula (a) is reduced in the presence of hydrogen and a catalytic hydrogen reduction catalyst to give a compound of formula (c) or formula (d).

Solvents usable in step B1 include chloroform, dichloromethane, and 1,2-dichloroethane. 1,2-Dichloroethane is preferred. [Ir(cod)pyr(PCy$_3$)]PF$_6$ (Crabtree's catalyst, Journal of Organic Chemistry, 51, 2655 (1986)) may be used as a catalyst in the catalytic hydrogen reduction. The reaction temperature may be 20° C. to 80° C. The reaction time may be 1 to 8 hr.

Solvents usable in step B2 include methanol, acetic acid, and mixed solvents thereof. A mixed solvent composed of methanol and acetic acid is preferred. Rh—Al$_2$O$_3$ may be used as a catalyst in the catalytic hydrogen reduction. The reaction temperature may be 0° C. to 40° C. The reaction time may be 1 to 8 hr.

Step C: Step of Construction of Side Chain of E-Isomer at 3-Position

[Chemical formula 5]

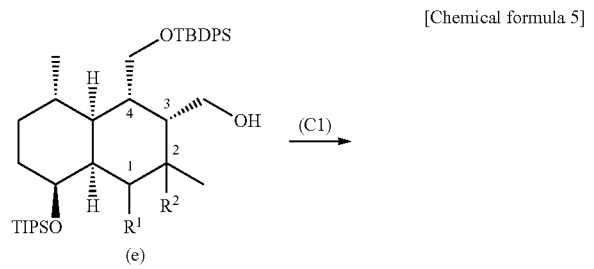

In step C, hydroxyl at the 3-position of the compound (b) obtained in step A or compound of formula (c) or (d) obtained in step B (these compounds being collectively represented by formula (e)) is oxidized to aldehyde, is then converted to a triple bond, and is further passed through two steps to give a compound of formula (j) of which the double bond is an E-isomer.

In step C1, hydroxyl at the 3-position is oxidized to aldehyde. Dichloromethane may be used as a solvent. 1,1,1-Triacetoxy-1,1-dihydro-1,2-benziodoxol-3(1H)-one may be used as an oxidizing agent. The reaction temperature may be 0° C. to 50° C. The reaction time may be 1 to 8 hr.

In step C2, the 3-position is dibromoethenylated. Solvents usable herein include dichloromethane and chloroform. Dichloromethane is preferred. Triphenylphosphine and carbon tetrabromide may be used as a reactant. The reaction temperature may be 0° C. to 50° C. The reaction time may be 1 to 8 hr.

In step C3, the 3-position is ethynylated. Tetrahydrofuran may be used as a solvent. n-Butyllithium may be used as a base. The reaction temperature may be −78° C. to −30° C. The reaction time may be 1 to 8 hr.

In step C4, the triple bond on the side chain at the 3-position is carbometalated and is then iodized. Dichloromethane may be used as a solvent. A combination of a zirconium catalyst $Cp_2ZrCl_2$ with trimethylaluminum may be used as a reactant. The reaction temperature may be −30° C. to 30° C. The reaction time may be 1 to 4 hr. Iodine may be used as a reactant in the iodination. Tetrahydrofuran may be used as a solvent. The reaction temperature may be −50° C. to 30° C. The reaction time may be 1 to 4 hr.

In step C5, an alkylation step and a deprotection step are carried out. Tetrahydrofuran may be used as a solvent in the alkylation step. A combination of a palladium catalyst $PdCl_2(PPh_3)_2$ with $(R_4)_2Zn$ may be used as a reactant for introducing alkyl. The reaction temperature may be −10° C. to 50° C. The reaction time may be 1 to 8 hr. Solvents usable in the deprotection step include tetrahydrofuran. Reagents usable in the deprotection include tetrabutylammonium fluoride. The reaction may be carried out under reflux. The reaction time may be 1 to 8 hr.

Step D: Step of Construction of Side Chain of Z-Isomer at 3-Position

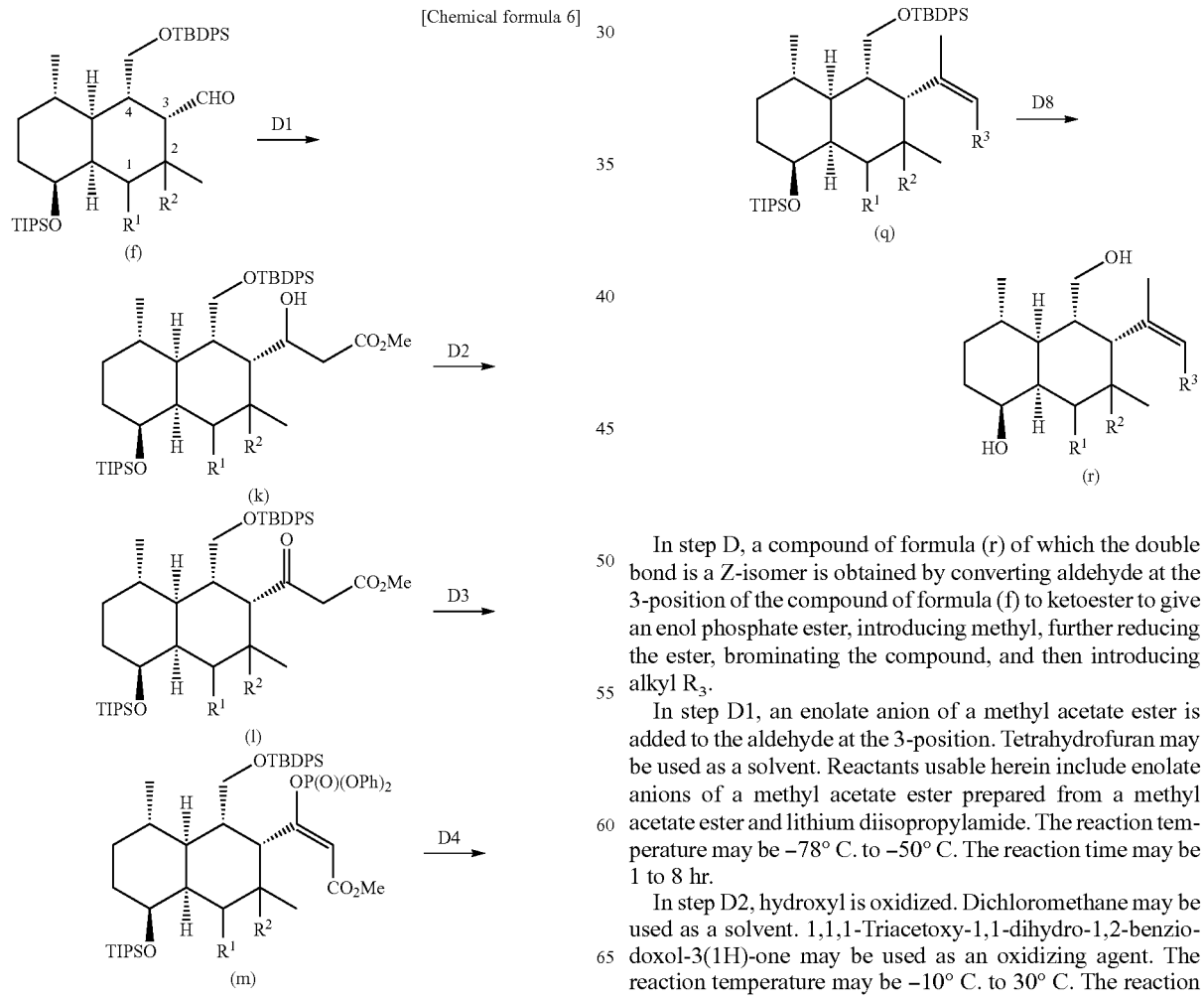

[Chemical formula 6]

In step D, a compound of formula (r) of which the double bond is a Z-isomer is obtained by converting aldehyde at the 3-position of the compound of formula (f) to ketoester to give an enol phosphate ester, introducing methyl, further reducing the ester, brominating the compound, and then introducing alkyl $R_3$.

In step D1, an enolate anion of a methyl acetate ester is added to the aldehyde at the 3-position. Tetrahydrofuran may be used as a solvent. Reactants usable herein include enolate anions of a methyl acetate ester prepared from a methyl acetate ester and lithium diisopropylamide. The reaction temperature may be −78° C. to −50° C. The reaction time may be 1 to 8 hr.

In step D2, hydroxyl is oxidized. Dichloromethane may be used as a solvent. 1,1,1-Triacetoxy-1,1-dihydro-1,2-benziodoxol-3(1H)-one may be used as an oxidizing agent. The reaction temperature may be −10° C. to 30° C. The reaction time may be 1 to 8 hr.

In step D3, an enol phosphate ester is synthesized. Hexamethylphosphoric triamide may be used as a solvent. Triethylamine and dimethylaminopyridine may be used as a base. ClP(O)(OPh)$_2$ may be used as a phosphorylating reagent. The reaction temperature may be −10° C. to 40° C. The reaction time may be 1 to 8 hr.

In step D4, methylation is carried out. N-methylpyrrolidone may be used as a solvent. A combination of a Fe(acac)$_3$ catalyst with MeMgCl may be used as a methylating reagent. The reaction temperature may be −20° C. to 40° C. The reaction time may be 1 to 8 hr.

In step D5, the ester is reduced. Dichloromethane may be used as a solvent. Diisobutylaluminium hydride may be used as a reducing agent. The reaction temperature may be −78° C. to −50° C. The reaction time may be 1 to 8 hr.

In step D6, bromination is carried out. Diethyl ether may be used as a solvent. Pyridine may be used as a base. Phosphorus tribromide may be used as a brominating reagent. The reaction temperature may be −20° C. to 40° C. The reaction time may be 1 to 8 hr.

In step D7, alkylation is carried out. When R$_3$ represents methyl, diethyl ether may be used as a solvent and lithium aluminum hydride may be used as a reducing agent. In this case, the reaction temperature may be −20° C. to 40° C., and the reaction time may be 1 to 8 hr. When R$_3$ represents C$_2$-C$_4$ alkyl, tetrahydrofuran and diethyl ether may be used as a solvent. Alkylating reagents usable herein include R$_3$MgCl, R$_3$MgBr, and R$_3$MgI. In this case, the reaction temperature may be −78° C. to 30° C., and the reaction time may be 1 to 8 hr.

In step D8, deprotection is carried out. Tetrahydrofuran may be used as a solvent. Tetrabutylammonium fluoride may be used as a deprotection reagent. The reaction may be carried out under reflux. The reaction time may be 1 to 8 hr.

Step E: Step of Conversion of 4-Position

[Chemical formula 7]

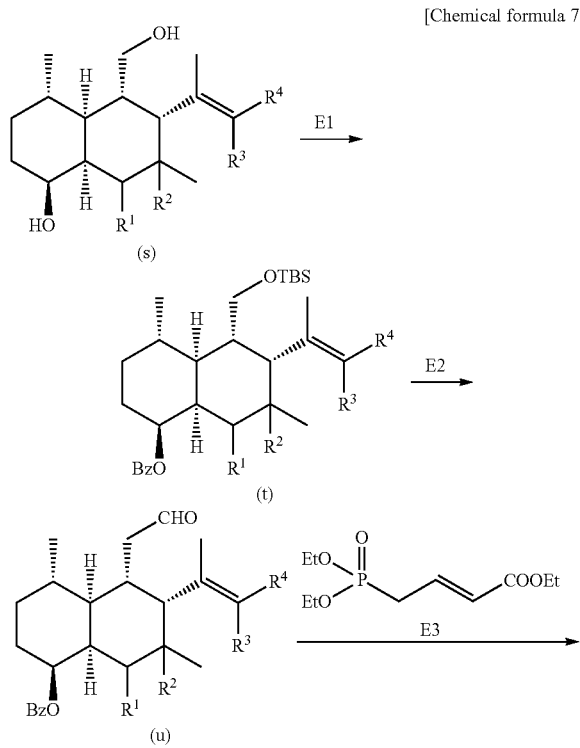

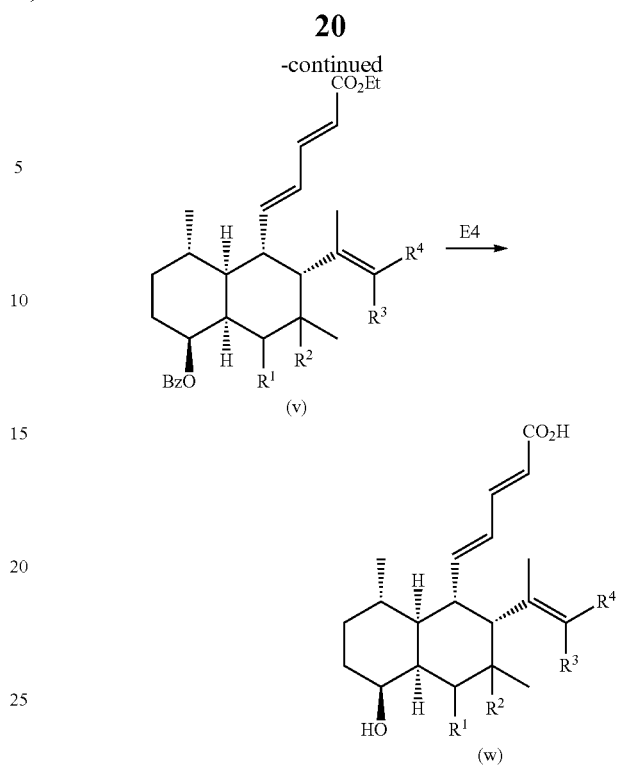

In step E, a diene side chain is introduced at the 4-position of the compound of formula (j) obtained in step C or the compound of formula (r) obtained in step D (these compounds being collectively represented by formula (s)) to give a compound of formula (w).

In step E1, hydroxyl is protected. Hydroxyl at the 4-position is first protected by tert-butyldimethylsilyl (TBS group). Dichloromethane may be used as a solvent. Imidazole may be used as a base. Tert-butyldimethylsilyl chloride may be used as a silylation reagent. The reaction temperature may be −10° C. to 40° C. The reaction time may be 1 to 8 hr. Hydroxyl at the 9-position is then protected by benzoyl. Dichloromethane may be used as a solvent. Dimethylaminopyridine may be used as a base. Benzoic anhydride may be used as a benzoylating reagent. The reaction temperature may be −10° C. to 40° C. The reaction time may be 1 to 8 hr.

In step E2, the protective group at the 4-position is removed, and the resultant hydroxyl is oxidized. Tetrahydrofuran may be used as a solvent in the deprotection step, Tetrabutylammonium fluoride may be used as a deprotection reagent. The reaction temperature may be −10° C. to 40° C. The reaction time may be 1 to 8 hr. Dichloromethane may be used as a solvent in the step of oxidizing the resultant hydroxyl at the 4-position. 1,1,1-Triacetoxy-1,1-dihydro-1,2-benziodoxol-3(1H)-one may be used as an oxidizing agent. The reaction temperature may be −10° C. to 30° C. The reaction time may be 1 to 8 hr.

In step E3, a diene side chain is synthesized. Tetrahydrofuran may be used as a solvent. Lithium hexamethyldisilazide may be used as a base. Phosphonic acid ester may be used as a reactant. The reaction temperature may be −78° C. to 30° C. The reaction time may be 1 to 8 hr.

In step E4, deprotection is carried out. A mixed solvent composed of ethanol and water may be used as a solvent. Preferably, the ratio of ethanol to water is 4:1. Lithium hydroxide may be used as a base. The reaction temperature may be −10° C. to 30° C. The reaction time may be 1 to 8 hr.

The compounds of formula (I) (specifically, the first group of compounds) may also be produced according to the following step F using MK8383 substance as a starting compound.

In step F, the double bond at the 1-position of MK8383 substance is selectively reduced to give compounds of formula (I).

"MK8383 substance" can be obtained by culturing microorganisms belonging to *Phoma* spp. (for example, a strain deposited under an accession number of FERM BP-6461) (Japanese Patent Application Laid-Open No. 126211/1995 and WO99/11596).

Step F when the MK8383 substance is used as the starting compound will be described below.

Step F

[Chemical formula 8]

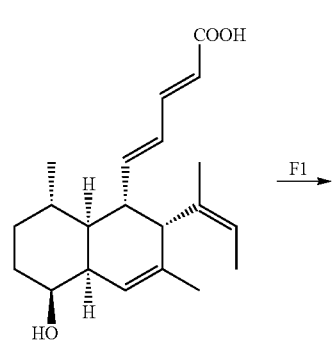

MK8383

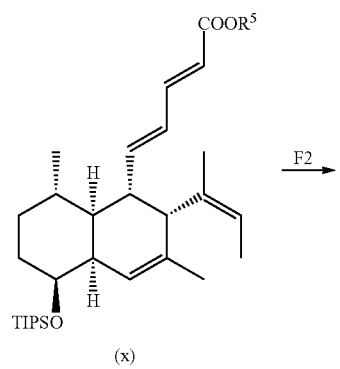

(x)

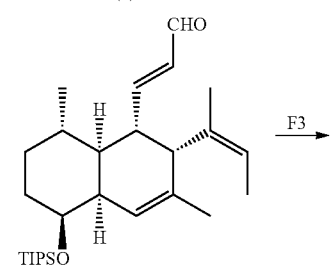

(y)

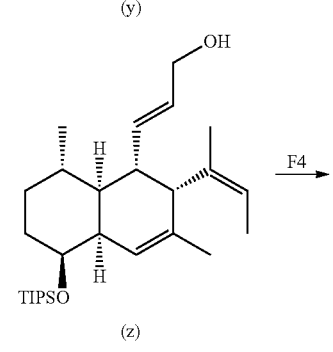

(z)

-continued

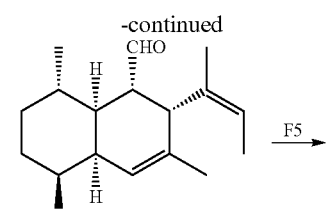

(aa)

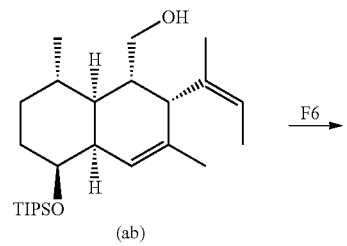

(ab)

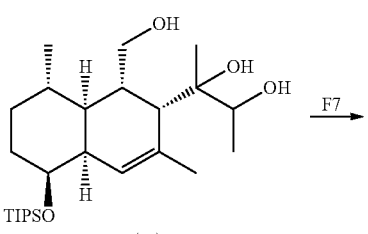

(ac)

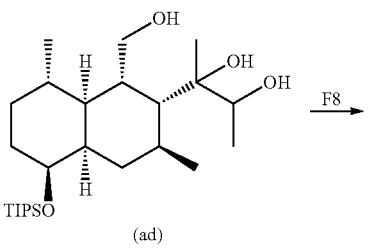

(ad)

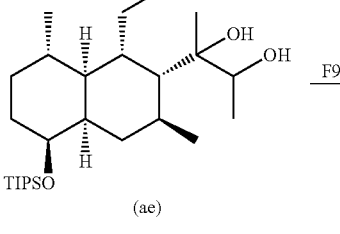

(ae)

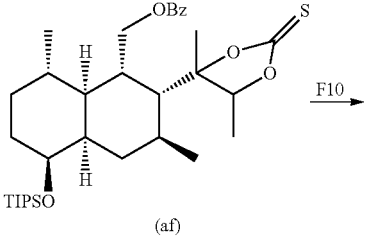

(af)

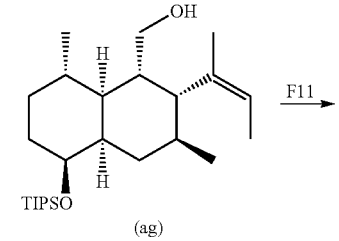

(ag)

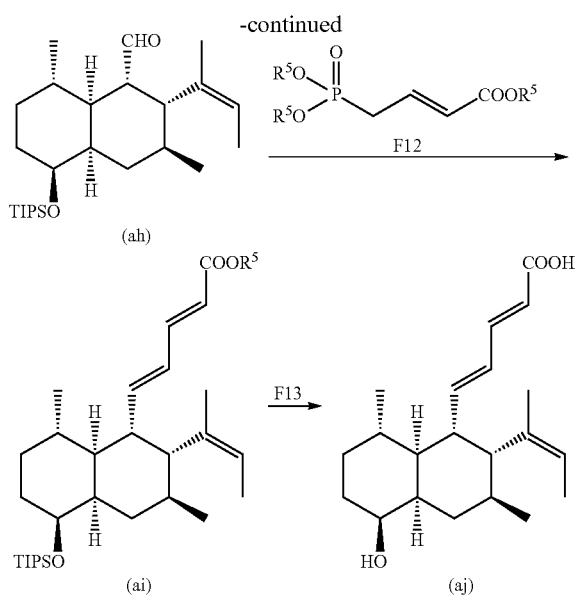

In step F1, the carboxylic acid in the MK8383 substance is esterified, and hydroxyl is protected by triIsopropylsilyl to give a compound of formula (x). In formula (x), $R^5$ represents $C_1$-$C_4$ alkyl.

The esterification reaction may be carried out according to the method described in T. W. Greene et. al, Protective groups in organic synthesis, third edition, 369, (1999), wiley-interscience. For example, in the synthesis of a methyl ester, methanol or mixed solvents such as methanol/benzene and methanol/toluene may be used as a solvent. Trimethylsilyldiazomethane may be used as a reactant. The reaction temperature may be −10° C. to 40° C. The reaction time may be 10 min to 4 hr.

Dichloromethane may be used as a solvent in the protection of hydroxyl by triisopropylsilyl. 2,6-Lutidine may be used as a base. Triisopropylsilyl trifluoromethanesulfonate may be used as a silylation reagent. The reaction temperature may be −10° C. to 40° C. The reaction time may be 10 min to 8 hr.

In step F2, the ester of the compound of formula (x) obtained in step F1 is reduced to alcohol, and diene at the 4-position is oxidatively cleaved and converted to an unsaturated aldehyde to give a compound of formula (y). Dichloromethane may be used as a solvent in the reduction reaction of the ester. Diisobutylaluminium hydride may be used as a reducing agent. The reaction temperature may be −78° C. to 30° C. The reaction time may be 5 min to 4 hr. A mixed solvent composed of dioxane and water may be used as a solvent in the convention of the diene to the unsaturated aldehyde. A combination of a catalytic amount of osmium tetroxide and sodium periodate may be used as an oxidizing agent. 2,6-Lutidine may be used as a base. The reaction temperature may be 0° C. to 30° C. The reaction time may be 30 min to 4 hr.

In step F3, the aldehyde of the compound of formula (y) is converted to alcohol to give a compound of formula (z). Dichloromethane may be used as a solvent. Diisobutylaluminum hydride may be used as a reducing agent. The reaction temperature may be −78° C. to 30° C. The reaction time may be 5 min to 4 hr.

In step F4, the double bond at the 4-position of the compound of formula (z) is oxidatively cleaved to aldehyde to convert the compound to a compound of formula (aa). A mixed solvent composed of dioxane and water may be used as a solvent. A combination of a catalytic amount of osmium tetroxide and sodium periodate may be used as an oxidizing agent. Pyridine may be used as a base. The reaction temperature may be 0° C. to 30° C. The reaction time may be 10 to 36 hr.

In step F5, the aldehyde of the compound of formula (aa) is converted to alcohol to give a compound of formula (ab). A mixed solvent composed of methanol and tetrahydrofuran may be used as a solvent. Sodium borohydride may be used as a reducing agent. The reaction temperature may be 0° C. to 30° C. The reaction time may be 5 min to 4 hr.

In step F6, the double bond at the 3-position of the compound of formula (ab) is converted to diol to give a compound of formula (ac). Pyridine may be used as a solvent. Osmium tetroxide may be used as an oxidizing agent. The reaction temperature may be 0° C. to 30° C. The reaction time may be 10 min to 4 hr.

In step F7, the double bond at the 1-position of the compound of formula (ac) is reduced in the presence of hydrogen and a catalytic hydrogen reduction catalyst to give a compound of formula (ad). Solvents usable herein include chloroform, dichloromethane, and 1,2-dichloroethane. Dichloromethane is preferred. [Ir(cod)pyr(PCy$_3$)]PF$_6$ may be used as a catalyst in the catalytic hydrogen reduction. The reaction temperature may be 30° C. to 80° C. The reaction time may be generally 30 min to 6 hr.

In step F8, hydroxyl at the 4-position of the compound of formula (ad) is protected by benzoyl to give a compound of formula (ae). Acetonitrile may be used as a solvent. Benzoyl cyanide may be used as a benzoylation reagent. Triethylamine may be used as a base. The reaction temperature may be −60° C. to 0° C. The reaction time may be generally 5 min to 2 hr.

In step F9, the diol on the side chain at the 3-position of the compound of formula (ae) is converted to a cyclic thiocarbonate to give a compound of formula (af). Toluene may be used as a solvent. Thiocarbonyldiimidazole may be used as a thiocarbonylation reagent. The reaction may be carried out under reflux. The reaction time may be 10 to 20 hr.

In step F10, the thiocarbonate at the 3-position of the compound of formula (af) is reduced, and the protective group of hydroxyl at the 4-position is removed by reduction to give a compound of formula (ag). Trimethyl phosphate may be used as a reducing agent in the reduction reaction of the thiocarbonate. When the reducing agent is used in an excessive amount, the reaction may be carried out in the absece of a solvent. The reaction may be carried out under reflux. The reaction time may be 30 to 80 hr. Dichloromethane may be used as a solvent in the deprotection reaction of benzoyl. Diisobutylaluminium hydride may be used as a reducing agent. The reaction temperature may be −78° C. to 0° C. The reaction time may be 5 min to 4 hr.

In step F11, in the same manner as in step E2 which is the oxidation step, hydroxyl at the 4-position of the compound of formula (ag) is oxidized to give a compound of formula (ah). Dichloromethane may be used as a solvent. A Dess-Martin Periodinate (Journal of Organic Chemistry 48, 4155 (1983)) may be used as an oxidizing agent. The reaction temperature may be 0° C. to 30° C. The reaction time may be generally 10 min to 2 hr.

In step F12, in the same reaction as in step E3, a diene side chain is introduced into the 4-position of the compound of formula (ah) to give a compound of formula (ai). In formula (ai), $R^5$ represents $C_1$-$C_4$ alkyl. Tetrahydrofuran may be used as a solvent. Lithium hexamethyldisilazide may be used as a base. Phosphonic acid ester may be used as a reactant. The reaction temperature may be −78° C. to 30° C. The reaction time may be 30 min to 8 hr.

In step F13, in the same reaction as in step E4, the two protective groups in the compound of formula (ai) are removed to give a compound of formula (aj) (that is, the compound of Example 3). A mixed solvent composed of ethanol and water may be used as a solvent in the deprotection reaction of the ester. Preferably, the mixed solvent has a mixing ratio of ethanol to water of 4:1. Lithium hydroxide may be used as a base. The reaction temperature may be −10° C. to 30° C. The reaction time may be 10 to 60 hr. Tetrahydrofuran may be used as a solvent in the deprotection reaction of silyl. Tetrabutylammonium fluoride may be used as a deprotecting agent. The reaction temperature may be 0° C. to 40° C. The reaction time may be 30 to 90 hr.

Agricultural and Horticultural Disease Control Agent

According to working examples, the compounds of the present invention have a high control effect, against plant pathogenic fungi, equivalent to MK8383 (Test Example 1) and, at the same time, have high photostability not possessed by MK8383 (Test Example 2). Thus, according to the present invention, there is provided an agricultural and horticultural disease control agent comprising a compound of the present invention as an active ingredient.

In the specification of the present application, the "agricultural and horticultural disease control agent" refers to an agent that exhibits control effect against plant diseases and includes agents that kills plant pathogenic microorganisms, as well as agents that suppress the growth of plant pathogenic microorganisms and agents that protect plants from infection with plant pathogenic microorganisms.

Agricultural and horticultural fungicides are preferred as the agricultural and horticultural disease control agent.

The plant pathogenic microorganisms as an object of the control in the present invention (microorganisms against which the compounds of the present invention exhibit control effect) is not particularly limited. Examples of such plant pathogenic microorganisms include plant pathogenic fungi and plant pathogenic bacteria. Preferred are plant pathogenic fungi.

Plant pathogenic fungi include, for example, *Alternaria alternata, Alternaria kikutiana, Botrytis cinerea, Cochliobolus miyabeanus, Colletotrichum atramentarium, Colletotrichum lagenarium, Fusarium oxysporum* f. sp. *cucumerinum, Fusarium oxysporum* f. sp. *lycopersici, Gibberella fujikuroi, Glomerella cingulata, Pyricularia oryzae, Rhizoctonia solani, Sclerotinia minor, Verticillium albo-atrum, Puccinia recondita, Erysiphe graminis, Phytophthora infestans, Pseudoperonospora cubensis, Sphaerotheca fuliginea, Alternaria solani, Sclerotinia sclerotiorum, Venturia inaequalis, Monilinia fructicola, Colletotrichum gloeosporioides, Cercospora kikuchii, Cercospora beticola,* and *Leptosphaeria nodorum*. Preferred are *Botrytis cinerea, Cercospora beticola, Rhizoctonia solani, Alternaria kikutiana, Colletotrichum lagenarium, Pyricularia oryzae,* and *Leptosphaeria nodorum*. More preferred is *Botrytis cinerea*.

When the compounds of the present invention are used as an active ingredient of the agricultural and horticultural disease control agent, the compounds of the present invention as such may be used. Alternatively, according to an ordinary method regarding the agricultural and horticultural disease control agent, the compound according to the present invention may be used as a mixture with suitable solid carriers, liquid carriers, gaseous carriers, surfactants, dispersants, or other adjuvants for preparations and formulated into any suitable dosage forms, for example, emulsifiable concentrates, liquid formulations, suspensions, wettable powders, dust formulations, granules, tablets, oils, aerosols, or floables.

Solid carriers include, for example, talc, bentonite, clay, kaolin, diatomaceous earth, vermiculite, white carbon, and calcium carbonate.

Liquid carriers include, for example, alcohols such as methanol, n-hexanol, and ethylene glycol; ketones such as acetone, methyl ethyl ketone, and cyclohexanone; aliphatic hydrocarbons such as n-hexane, kerosine, and kerosene; aromatic hydrocarbons such as toluene, xylene, and methylnaphthalene; ethers such as diethyl ether, dioxane, and tetrahydrofuran; esters such as ethyl acetate; nitriles such as acetonitrile and isobutyronitrile; acid amides such as dimethylformamide and dimethylacetamide; vegetable oils such as soy bean oil and cotton seed oil; dimethylsulfoxide; and water.

Gaseous carriers include, for example, LPG, air, nitrogen, carbon dioxide, and dimethyl ether.

Surfactants or dispersants include, for example, alkylsulfuric esters, alkyl(aryl)sulfonic acid salts, polyoxyalkylene alkyl(aryl)ethers, polyhydric alcohol esters, and lignin sulfonic acid salts.

Adjuvants for preparations include, for example, carboxymethylcellulose, gum arabic, polyethylene glycol, and calcium stearate.

The above carriers, surfactants, dispersants, and adjuvants may be used either solely or in combination according to need.

The content of the active ingredient in preparations is not particularly limited, but is generally 1 to 50% by weight for emulsifiable concentrate, 1 to 50% by weight for wettable powder, 0.1 to 30% by weight for dust formulation, 0.1 to 15% by weight for granules, 0.1 to 10% by weight for oils, and 0.1 to 10% by weight for aerosols.

The agricultural and horticultural disease control agent according to the present invention as such may be used or alternatively may, if necessary, be diluted before use.

The agricultural and horticultural disease control agent according to the present invention may also be used together with other harmful organism control agents. For example, the agricultural and horticultural disease control agent may be applied as a mixture or alternatively may be applied sequentially or simultaneously with other agents. Other harmful organism control agents mixable with the agricultural and horticultural disease control agent include, for example, fungicides, insecticides, miticides, herbicides, plant growth-regulating agents, and fertilizers, specifically those described, for example, in The Pesticide Manual, the 13th edition, published by The British Crop Protection Council and SHIBUYA INDEX, the 12th edition, 2007, published by SHIBUYA INDEX RESEARCH GROUP.

Insecticides usable as a mixture with the agricultural and horticultural disease control agent according to the present invention include, for example, acephate, dichlorvos, EPN, fenitrothion, fenamifos, prothiofos, profenofos, pyraclofos, chlorpyrifos-methyl, chlorfenvinphos, demeton, ethion, malathion, coumaphos, isoxathion, fenthion, diazinon, thiodicarb, aldicarb, oxamyl, propoxur, carbaryl, fenobucarb, ethiofencarb, fenothiocarb, pirimicarb, carbofuran, carbosulfan, furathiocarb, hyquincarb, alanycarb, methomyl, benfuracarb, cartap, thiocyclam, bensultap, dicofol, tetradifon, acrinathrin, bifenthrin, cycloprothrin, cyfluthrin, dimefluthrin, empenthrin, fenfluthrin, fenpropathrin, imiprothrin, metofluthrin, permethrin, phenothrin, resmethrin, tefluthrin, tetramethrin, tralomethrin, transfluthrin, cypermethrin, deltamethrin, cyhalothrin, fenvalerate, fluvalinate, ethofenprox, flufenprox, halfenprox, silafluofen, cyromazine, diflubenzuron, teflubenzuron, flucycloxuron, flufenoxuron, hexaflumuron, lufenuron, novaluron, penfluoron, triflumuron, chlorfluazuron, diafenthiuron, methoprene, fenoxycarb, pyriproxyfen, halofenozide, tebufenozide, methoxyfenozide, chromafenozide, dicyclanil, buprofezin, hexythiazox, amitraz, chiordimeform, pyridaben, fenpyroximate, flufenerim, pyrimidifen, tebufenpyrad, tolfenpyrad, fluacrypyrim, acequinocyl, cyflumetofen, flubendiamide, ethiprole, fipronil, ethoxazole, imidacloprid, nitenpyram, clothianidin, acetamiprid, dinotefuran, thiacloprid, thiamethoxam, pymetrozine, bifenazate, spirodiclofen, spiromesifen, flonicamid, chlorfenapyr, pyriproxyfene, indoxacarb, pyridalyl, spinosad, avermectin, milbemycin, azadirachtin, nicotine, rotenone, BT formulations, insect pathological viral agents, emamectinbenzoate, spinetoram, pyrifluquinazon, chlorantraniliprole, cyantraniliprole, cyenopyrafen, spirotetramat, lepimectin, metaflumizone, pyrafluprole, pyriprole, dimefluthrin, fenazaflor, hydramethylnon, and triazamate.

Fungicides usable as a mixture with the agricultural and horticultural disease control agent according to the present invention include, for example, strobilrin compounds such as azoxystrobin, kresoxym-methyl, trifloxystrobin, orysastrobin, picoxystrobin, and fuoxastrobin; anilinopyrimidine compounds such as mepanipyrim, pyrimethanil, and cyprodinil; azole compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline compounds such as quinomethionate; dithiocarbamate compounds such as maneb, zineb, mancozeb, polycarbamate, and propineb; phenylcarbamate compounds such as diethofencarb; organochlorine compounds such as chlorothalonil and quintozene; benzimidazole compounds such as benomyl, thiophanate-methyl, and carbendazole; phenylamide compounds such as metalaxyl, oxadixyl, ofurase, benalaxyl, furalaxyl, and cyprofuram; sulfenic acid compounds such as dichlofluanid; copper compounds such as copper hydroxide and oxine-copper; isoxazole compounds such as hydroxyisoxazole; organophosphorus compounds such as fosetyl-aluminium and tolclofos-methyl; N-halogenothioalkyl compounds such as captan, captafol, and folpet; dicarboxylmide compounds such as procymidone, iprodione, and vinchlozolin; benzanilide compounds such as flutolanil and mepronil; morpholine compounds such as fenpropimorph and dimethomorph; organotin compounds such as fenthin hydroxide and fenthin acetate; and cyanopyrrole compounds such as fludioxonil and fenpiclonil. Other fungicides include fthalide, probenazole, acibenzolar-S-methyl, tiadinil, isotianil, carpropamid, diclocymet, fenoxanil, tricyclazole, pyroquilon, ferimzone, fluazinam, cymoxanil, triforine, pyrifenox, fenarimol, fenpropidin, pencycuron, cyazofamid, cyflufenamid, boscalid, penthiopyrad, proquinazid, quinoxyfen, famoxadone, fenamidone, iprovalicarb, benthiavalicarb-isopropyl, fluopicolide, pyribencarb, flutianil, isopyrazam, kasugamycin, or validamycin.

Miticides usable as a mixture with the agricultural and horticultural disease control agent according to the present invention include, for example, bromopropylate, tetradifon, propargite, amitraz, fenothiocarb, hexythiazox, fenbutatin oxide, dienochlor, fenpyroximate, tebufenpyrad, pyridaben, pyrimidifen, clofentezine, etoxazole, halfenprox, milbemectin, acequinocyl, bifenazate, fluacrypyrim, spirodichlofen, spiromesifen, chlorfenapyr, Avermectin, cyenopyrafen, and cyflumetofen.

Herbicides usable as a mixture with the agricultural and horticultural disease control agent according to the present invention include, for example, phenoxy acid compounds such as cyhalofop-butyl and 2,4-D; carbamate compounds such as esprocarb and desmedipham; acid amide compounds such as alachlor and metolachlor; urea compounds such as diuron and tebuthiuron; sulfonylurea compounds such as halosulfuron and flazasulfuron; pyrimidyloxybenzoic acid compounds such as pyriminobac-methyl; and amino acid compounds such as glyphosate, bilanafos, and glufosinate-ammonium.

Plant growth-regulating agents usable as a mixture with the agricultural and horticultural disease control agent according to the present invention include, for example, ethylene agents such as ethephon; auxin agents such as indolebutyric acid and ethychlozate; cytokinin agents; gibberellin agents; auxin antagonists; growth retardants; and antidesiccants.

Fertilizers usable as a mixture with the agricultural and horticultural disease control agent according to the present invention include, for example, nitrogenous fertilizers such as urea, ammonium nitrate, ammonium magnesia nitrate, and ammonium chloride; phosphate fertilizers such as calcium superphosphate, ammonium phosphate, magnesia superphosphate, and magnesia phosphate; potassic fertilizers such as potassium chloride, potassium bicarbonate, potassium magnesia nitrate, potassium nitrate, and potassium sodium nitrate; manganous fertilizers such as manganese sulfate and manganese magnesia nitrate; and boric fertilizers such as boric acid and borate salt.

Methods usable for applying the agricultural and horticultural disease control agent according to the present invention are not particularly limited as long as the method can generally be applied in agriculture and horticulture and include, for example, foliage application, water-surface application, soil treatment, seedling box application, and seed disinfection.

The amount of the agricultural and horticultural disease control agent according to the present invention applied may be determined depending upon the type and severity of pathogenesis of object diseases, the type and object sites of object crops, application methods generally adopted in agriculture and horticulture, and other application forms such as aerial spray and ultralow-volume spray. When the agricultural and horticultural disease control agent according to the present invention is applied to foliages of plants, for emulsifiable concentrates, wettable powders, and floables, a solution obtained by diluting 1 to 1000 g of the preparation with 50 to 1000 liters of water may be used per 10 ares; and, for dust formaulations, approximately 1 to 10 kg thereof per 10 ares may be used. For example, a method may be adopted in which 100 g of a preparation containing 20% by weight of compound 1 is diluted with 200 liters of water, and the whole quantity of the solution per 10 ares may be applied to a field. When the agricultural and horticultural disease control agent according to the present invention is applied to soil, approximately 1 to 10 kg per 10 ares of granules may be used.

According to the present invention, there is provided a process for producing a compound according to the present invention.

Further, according to the present invention, there is provided an intermediate of a compound according to the present invention.

EXAMPLES

The present invention is further illustrated by the following Examples that are not intended as a limitation of the invention.

In Examples 1 to 3, $^1$H-NMR and $^{13}$C-NMR spectra were measured with spectrometers BRUKER AVANCE 600, JEOL Lambda 500, and JEOL AL 400. Tetramethylsilane was used as an internal standard.

JEOL JMS-SX102A was used for mass spectrum measurement.

For thin-layer chromatography, TLC 60E-254 (manufactured by Merck Ltd.) was used, and a UV lamp and phosphomolybdic acid were used for detection.

Silica Gel 60N (spherical, neutral) 63-210 (manufactured by KANTO CHEMICAL CO., INC.) and Silica Gel 60N (spherical, neutral) 40-50 μm (manufactured by KANTO CHEMICAL CO., INC.) were used for chromatography on silica gel.

Starting compound 1 was a compound synthesized according to the description of Org. Letters, 2004, 6, 553-556, and starting compound 2 was purchased from Aldrich.

[Chemical formula 9]

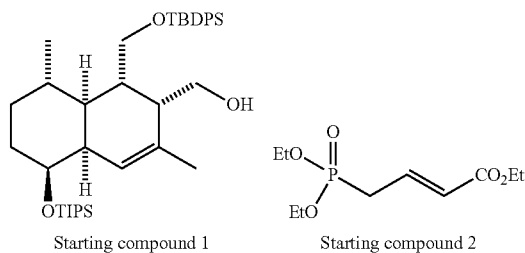

Starting compound 1     Starting compound 2

In structural formulae in the specification of the present application, TIPS represents triisopropylsilyl, TBDPS represents tert-butyldiphenylsilyl, TBS represents tert-butyldimethylsilyl, Bz represents benzoyl, Et represents ethyl, Ph represents phenyl, acac represents acetylacetonato, Hex represents n-hexane, and AcOEt represents ethyl acetate. Further, in the specification of the present application, TIPSOTf represents triisopropylsilyl trifluoromethanesulfonate, DIBAL represents diisobutylaluminium hydride, TCDI represents thiocarbonyldiimidazole, DMAP represents N,N-dimethyl-4-aminopyridine, TBAF represents tetrabutylammonium fluoride, and LiHMDS represents Lithium hexamethyldisilazide.

Example 1

Synthesis of (2E,4E)-5-{(1aR,2R,3S,3aS,4S,7S,7aS,7bR)-2-[(E)-but-2-en-2-yl]-decahydro-7-hydroxy-1a,4-dimethyl-1H-cyclopropa[a]naphthalen-3-yl}penta-2,4-dienoic acid Production Step 1-(1)

$Et_2Zn$ (0.428 ml, 0.423 mmol) and $CH_2I_2$ (0.0398 ml, 0.479 mmol) were added in that order to a solution (1.5 ml) of a starting compound 1 (0.0443 g, 0.0698 mmol) in $(CH_2Cl)_2$ at 0° C. under an argon atmosphere. The mixture was then heated to 35° C. and was stirred. The above procedure was further repeated every five hours four times. After the disappearance of the starting compound was confirmed by TLC, a saturated aqueous $NH_4Cl$ solution and a saturated aqueous $NaHCO_3$ solution were added in that order, followed by separation. The aqueous layer was extracted with $CH_2Cl_2$, and the collected oil layer was dried over $Na_2SO_4$. The dried oil layer was filtered, and the solvent was then removed under the reduced pressure. The residue was purified by column chromatography on silica gel (Hex:AcOEt=15:1) to give the following compound (0.0426 g, 94%).

$R_f$ 0.38 (Benzen:AcOEt=100:1, 2 times eluent); $^1$H NMR (400 MHz, $CDCl_3$) δ 7.70-7.59 (4H, m), 7.49-7.35 (6H, m), 4.00-3.85 (1H, m), 3.81-3.65 (2H, m), 3.65-3.57 (1H, m), 3.54-3.40 (1H, m), 3.23 (1H, dd, J=10.7, 2.7 Hz), 2.36-2.25 (1H, m), 2.11-2.00 (1H, m), 1.72-1.58 (5H, m), 1.45-1.28 (2H, m), 1.10-0.89 (33H, m), 0.85 (3H, d, J=6.3 Hz), 0.69-0.61 (1H, m), 0.38-0.31 (1H, m), −0.05--0.11 (1H, m).

[Chemical formula 10]

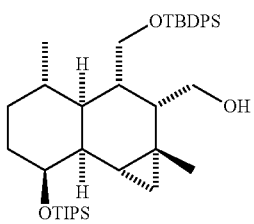

Production Step 1-(2)

A Dess-Martin reagent (0.0859 g, 0.203 mmol) was added to a solution (1.5 ml) of the compound (0.0426 g, 0.0656 mmol) obtained in production step 1-(1) in $CH_2Cl_2$ under an argon atmosphere, and the mixture was stirred at room temperature. After the completion of the reaction, the reaction solution was diluted with $Et_2O$, and a saturated aqueous $Na_2S_2O_3$ solution and a saturated aqueous $NaHCO_3$ solution were added to the diluted solution, followed by separation. The aqueous layer was extracted with $Et_2O$, and the collected oil layer was dried over $MgSO_4$. The dried oil layer was filtered, and the solvent was then removed under the reduced pressure. The residue was purified by column chromatography on silica gel (Hex:AcOEt=50:1) to give the following compound (0.0391 g, 92%).

$R_f$ 0.56 (Hex:AcOEt=4:1); $^1$H NMR (400 MHz, $CDCl_3$) δ 9.75 (1H, d, J=2.4 Hz), 7.66-7.56 (4H, m), 7.57-7.33 (6H, m), 3.78-3.69 (1H, m), 3.68-3.58 (1H, m), 3.44-3.37 (1H, m), 2.57-2.47 (1H, m), 1.84-1.76 (1H, m), 1.74-1.57 (2H, m), 1.34-1.24 (1H, m), 1.11-0.93 (37H, m), 0.85 (3H, d, J=6.6 Hz), 0.82-0.74 (1H, m), 0.68-0.61 (1H, m), 0.31-0.25 (1H, m).

[Chemical formula 11]

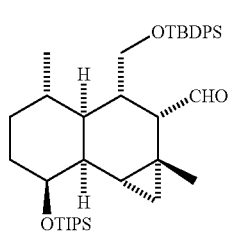

Production Step 1-(3)

$PPh_3$ (0.0540 g, 0.206 mmol) was added to a solution (0.5 ml) of $CBr_4$ (0.0288 g, 0.0868 mmol) in $CH_2Cl_2$ under an argon atmosphere, and the mixture was stirred at room temperature for 10 min. A solution (1 ml) of the compound (0.0316 g, 0.0488 mmol) obtained in production step 1-(2) in $CH_2Cl_2$ was added thereto, and the mixture was stirred at room temperature. After one hr from the start of the mixture, a solution prepared by adding $PPh_3$ (0.0543 g, 0.207 mmol) to a solution (0.5 ml) of $CBr_4$ (0.0291 g, 0.0877 mmol) in $CH_2Cl_2$ and stirring the mixture at room temperature for 10 min was added to the reaction solution, and the mixture was stirred at room temperature. After the completion of the reaction, a saturated aqueous $NaHCO_3$ solution was added to the reaction solution, followed by separation. The aqueous layer was extracted with CH$_2$Cl$_2$, and the collected oil layer was dried over Na$_2$SO$_4$. The dried oil layer was filtered, and the solvent was then removed under the reduced pressure to precipitate a solid. The residue was diluted with hexane, and the solid was removed by filtration. Hexane was removed under the reduced pressure. The residue was purified by column chromatography on silica gel (Hex:AcOEt=100:1) to give the following compound (0.0307 g, 78%).

R$_f$ 0.38 (Hex:AcOEt=30:1); $^1$H NMR (400 MHz, CDCl$_3$) δ 7.69-7.58 (4H, m), 7.48-7.33 (6H, m), 6.18 (1H, d, J=9.3 Hz), 3.89-3.79 (1H, m), 3.56-3.44 (2H, m), 2.79-2.73 (1H, m), 2.37-2.26 (1H, m), 2.10-2.00 (1H, m), 1.80-1.64 (2H, m), 1.47-1.34 (2H, m), 1.02-0.95 (35H, m), 0.95-0.80 (4H, m), 0.43-0.33 (1H, m), 0.45--0.04 (1H, m).

[Chemical formula 12]

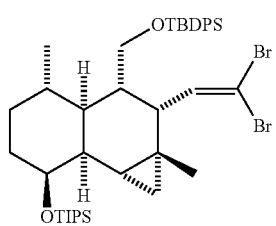

Production Step 1-(4)

A hexane solution (0.0750 ml, 1.58 M) of n-BuLi was added to a solution (1 ml) of the compound (0.0307 g, 0.0382 mmol) obtained in production step 1-(3) in THF at −78° C. under an argon atmosphere, and the mixture was stirred for 15 min. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=100:1) to give the following compound (0.0246 g, 96%).

R$_f$ 0.49 (Hex:AcOEt=20:1); $^1$H NMR (400 MHz, CDCl$_3$) δ 7.72-7.61 (4H, m), 7.45-7.33 (6H, m), 3.94-3.86 (1H, m), 3.83-3.74 (1H, m), 3.65-3.57 (1H, m), 2.98-2.92 (1H, m), 2.12-2.05 (1H, m), 2.05-1.98 (2H, m), 1.73-1.57 (3H, m), 1.16 (3H, s), 1.10-0.98 (33H, m), 0.86-0.79 (1H, m) 0.77 (3H, d, J=6.6 Hz), 0.48-0.42 (1H, m), 0.40-0.32 (1H, m).

[Chemical formula 13]

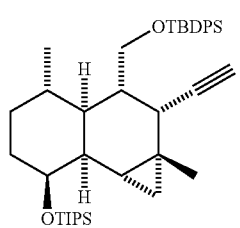

Production Step 1-(5)

A hexane solution (1.06 ml, 1.03 M) of Me$_3$Al was added to a solution (0.4 ml) of Cp$_2$ZrCl$_2$ (0.107 g, 0.365 mmol) in CH$_2$Cl$_2$ at 0° C. under an argon atmosphere, and the mixture was stirred at room temperature for 30 min. The mixture was then cooled to −30° C., and H$_2$O (0.0066 ml, 0.367 mmol) was added to the cooled solution. The mixture was heated to −10° C. and was stirred for 10 min. The reaction solution was again cooled to −30° C. A solution (1 ml) of the compound (0.0235 g, 0.0365 mmol) obtained in production step 1-(4) in CH$_2$Cl$_2$ was added to the cooled solution, and the mixture was stirred for one hr. After the disappearance of the starting compound was confirmed by TLC, a solution (1 ml) of I$_2$ (0.139 g, 0.546 mmol) in THF was added thereto, and the mixture was stirred for half a day. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=100:1) to give the following compound (0.0266 g, 93%).

R$_f$ 0.42 (Hex:AcOEt=20:1); $^1$H NMR (400 MHz, CDCl$_3$) δ 7.65-7.54 (4H, m), 7.46-7.33 (6H, m), 6.12 (1H, s), 3.89-3.78 (1H, m), 3.39 (1H, dd, J=10.2, 10.2 Hz), 3.18 (1H, dd, J=10.2, 3.7 Hz), 2.45 (1H, d, J=6.1 Hz), 2.26-2.13 (1H, m), 2.08-1.95 (1H, m), 1.80-1.45 (9H, m), 1.14-0.99 (30H, m), 0.98 (3H, s), 0.88 (3H, d, J=6.3 Hz), 0.81-0.72 (1H, m), 0.65-0.55 (1H, m), 0.16-0.09 (1H, m).

[Chemical formula 14]

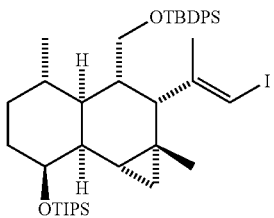

Production Step 1-(6)

A THF solution (0.0508 ml, 1.0 M) of Me$_2$Zn was gradually added dropwise to a solution (1 ml) of PdCl$_2$(PPh$_3$)$_2$ (0.0266 g, 0.00256 mmol) and the compound (0.0266 g, 0.0339 mmol) obtained in production step 1-(5) in THF under an argon atmosphere, and the mixture was stirred at room temperature. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=150:1) to give the following compound (0.0220 g, 96%).

R$_f$ 0.59 (Hex:AcOEt=30:1); $^1$H NMR (400 MHz, CDCl$_3$) δ 7.64-7.56 (4H, m), 7.45-7.31 (6H, m), 5.43 (1H, d, J=5.9 Hz), 3.90-3.80 (1H, m), 3.40 (1H, dd, J=10.2, 10.2 Hz), 3.24 (1H, dd, J=10.2, 4.6 Hz), 2.26-2.20 (1H, m), 2.20-2.12 (1H, m), 2.08-2.01 (1H, m), 1.76-1.64 (3H, m), 1.44 (3H, d, J=5.9 Hz), 1.34 (3H, s), 1.13-0.96 (33H, m), 0.95 (3H, s), 0.89 (3H, d, J=6.1 Hz), 0.72-0.64 (1H, m), 0.59-0.51 (1H, m), 0.12-0.08 (1H, m).

[Chemical formula 15]

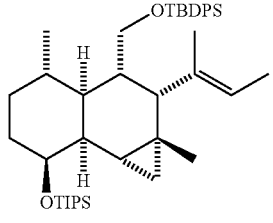

Production Step 1-(7)

A THF solution (0.490 ml, 1.0 M) of TBAF was added to a solution (1 ml) of the compound (0.0220 g, 0.0327 mmol)

obtained in production step 1-(6) in THF under an argon atmosphere, and the mixture was stirred with heating under reflux. After the completion of the reaction, a saturated aqueous NH₄Cl solution was added to the reaction solution, followed by separation. The aqueous layer was extracted with Et₂O, and the collected oil layer was dried over Na₂SO₄. The dried oil layer was filtered, and the solvent was then removed under the reduced pressure. The residue was purified by column chromatography on silica gel (Hex:AcOEt=1:2) to give the following compound (0.0085 g, 93%).

$R_f$ 0.11 (Hex:AcOEt=1:1); ¹H NMR (400 MHz, CDCl₃) δ 5.72-5.63 (1H, m), 3.84-3.74 (1H, m), 3.53-3.43 (1H, m), 3.36-3.26 (1H, m), 2.35 (1H, d, J=6.8 Hz), 2.24-2.14 (1H, m), 1.98-1.90 (1H, m), 1.81-1.71 (4H, m), 1.69 (3H, s), 1.66 (3H, d, J=6.3 Hz), 1.48-1.36 (1H, m), 1.14-1.03 (1H, m), 1.01 (3H, s), 0.91 (3H, d, J=6.3 Hz), 0.72 (1H, dd, J=8.8, 5.1 Hz), 0.60-0.52 (1H, m), 0.38-0.33 (1H, m).

[Chemical formula 16]

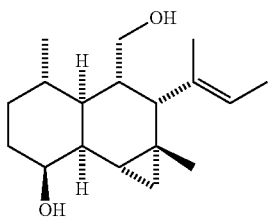

Production Step 1-(8)

Imidazole (0.0077 g, 0.113 mmol) and TBSCl (0.0528 g, 0.350 mmol) were added in that order to a solution (1 ml) of the compound (0.0085 g, 0.0319 mmol) obtained in production step 1-(7) in CH₂Cl₂ under an argon atmosphere, and the mixture was stirred at room temperature. After the completion of the reaction, a saturated aqueous NH₄Cl solution was added to the reaction solution, followed by separation. The aqueous layer was extracted with CH₂Cl₂, and the collected oil layer was dried over Na₂SO₄. The dried oil layer was filtered, and the solvent was then removed under the reduced pressure. The residue was purified by column chromatography on silica gel (Hex:AcOEt=10:1) to give the following compound (0.0079 g, 65%).

$R_f$ 0.76 (Hex:AcOEt=1:1); ¹H NMR (400 MHz, CDCl₃) δ 5.61-5.50 (1H, m), 3.82-3.70 (1H, m), 3.31-3.20 (2H, m), 2.36-2.26 (1H, m), 2.19-2.06 (1H, m), 2.02-1.93 (1H, m), 1.80-1.58 (7H, m), 1.45-1.36 (2H, m), 1.00 (3H, s), 0.93-0.79 (15H, m), 0.72-0.62 (1H, m), 0.58-0.49 (1H, m), 0.28-0.21 (1H, m), 0.03--0.08 (6H, m).

[Chemical formula 17]

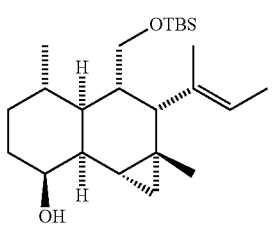

Production Step 1-(9)

DMAP (0.0251 g, 0.205 mmol) and Bz₂O (0.0293 g, 0.130 mmol) were added in that order to a solution (1 ml) of the compound (0.0079 g, 0.0201 mmol) obtained in production step 1-(8) in CH₂Cl₂ under an argon atmosphere, and the mixture was stirred at room temperature. After the completion of the reaction, a saturated aqueous NH₄Cl solution was added to the reaction solution, followed by separation. The aqueous layer was extracted with CH₂Cl₂, and the collected oil layer was dried over Na₂SO₄. The dried oil layer was filtered, and the solvent was then removed under the reduced pressure. The residue was purified by column chromatography on silica gel (Hex:AcOEt=50:1) to give the following compound (0.0102 g, quant.).

$R_f$ 0.57 (Hex:AcOEt=10:1); ¹H NMR (400 MHz, CDCl₃) δ 8.13-8.01 (2H, m), 7.60-7.50 (1H, m), 7.49-7.39 (2H, m), 5.60-5.51 (1H, m), 5.16-5.06 (1H, m), 3.29-3.21 (2H, m), 2.35 (1H, d, J=6.3 Hz), 2.23-2.06 (2H, m), 2.01-1.90 (1H, m), 1.87-1.72 (2H, m), 1.69-1.58 (6H, m), 1.56-1.44 (2H, m), 1.30-1.15 (1H, m), 1.04 (3H, s), 0.92 (3H, d, J=5.1 Hz), 0.88-0.82 (9H, m), 0.79-0.71 (1H, m), 0.69-0.62 (1H, m), 0.27-0.19 (1H, m), 0.02--0.07 (6H, m).

[Chemical formula 18]

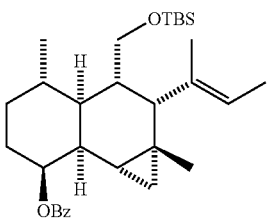

Production Step 1-(10)

A THF solution (0.185 ml, 1.0 M) of TBAF was added to a solution (0.5 ml) of the compound (0.0102 g, 0.0205 mmol) obtained in production step 1-(9) in THF under an argon atmosphere, and the mixture was stirred with heating under reflux for half a day. After the completion of the reaction, a saturated aqueous NH₄Cl solution was added to the reaction solution, followed by separation. The aqueous layer was extracted with Et₂O, and the collected oil layer was dried over Na₂SO₄. The dried oil layer was filtered, and the solvent was then removed under the reduced pressure. The residue was purified by column chromatography on silica gel (Hex:AcOEt=4:1) to give the following compound (0.0063, 80%).

$R_f$ 0.18 (Hex:AcOEt=4:1); ¹H NMR (400 MHz, CDCl₃) δ 8.12-8.03 (2H, m), 7.60-7.52 (1H, m), 7.49-7.40 (2H, m), 5.71-5.62 (1H, m), 5.17-5.08 (1H, m), 3.54-3.42 (1H, m), 3.36-3.25 (1H, m), 2.37 (1H, d, J=6.8 Hz), 2.37-2.12 (2H, m), 1.98-1.91 (1H, m), 1.89-1.76 (2H, m), 1.69 (3H, s), 1.65 (3H, d, J=6.8 Hz), 1.42-1.35 (1H, m), 1.31-1.18 (2H, m), 1.04 (3H, s), 0.95 (3H, d, J=6.3 Hz), 0.79-0.72 (1H, m), 0.70-0.64 (1H, m), 0.34-0.28 (1H, m).

[Chemical formula 19]

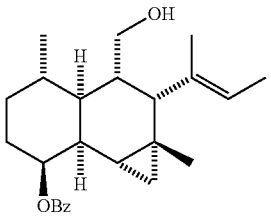

Production Step 1-(11)

A Dess-Martin reagent (0.0211 g, 0.0497 mmol) was added to a solution (0.8 ml) of the compound (0.0063 g, 0.0165 mmol) obtained in production step. 1-(10) in CH₂Cl₂ under an argon atmosphere, and the mixture was stirred at room temperature. After the completion of the reaction, the reaction solution was diluted with Et₂O, and a saturated aqueous Na₂S₂O₃ solution and a saturated aqueous NaHCO₃ solution were added to the diluted solution, followed by separation. The aqueous layer was extracted with Et₂O, and the collected oil layer was dried over Na₂SO₄. The dried oil layer was filtered, and the solvent was then removed under the reduced pressure. The residue was purified by column chromatography on silica gel (Hex:AcOEt=20:1) to give the following compound (0.0063 g, 100%).

$R_f$ 0.60 (Hex:AcOEt=4:1); $^1$H NMR (400 MHz, CDCl$_3$) δ 9.65 (1H, d, J=1.7 Hz), 8.10-8.01 (2H, m), 7.59-7.51 (1H, m), 7.50-7.40 (2H, m), 5.74 (1H, q, J=6.6 Hz), 5.12 (1H, ddd, J=11.2, 4.9, 4.9 Hz), 2.67-2.57 (2H, m), 2.16-2.08 (1H, m), 2.04-1.94 (1H, m), 1.88-1.72 (3H, m), 1.71 (3H, s), 1.68 (3H, d, J=6.6 Hz), 1.32-1.15 (2H, m), 1.14 (3H, s), 0.91 (3H, d, J=6.3 Hz), 0.87-0.76 (2H, m), 0.10 (1H, dd, J=4.4, 4.4 Hz).

[Chemical formula 20]

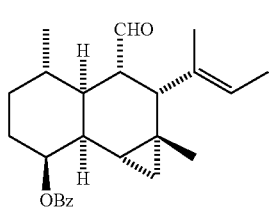

Production Step 1-(12)

A THF solution (0.0387 ml, 1.07 M) of LiHMDS was gradually added dropwise to a solution (0.3 ml) of a starting compound 2 (0.0169 g, 0.0675 mmol) in THF at −78° C. under an argon atmosphere, and the mixture was stirred for 30 min. A solution (1 ml) of the compound (0.0063 g, 0.0166 mmol) obtained in production step 1-(11) in THF was added to thereto, and the mixture was stirred for 2 hr. The mixture was then heated to 0° C. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=20:1). After $^1$H-NMR measurement, the compound, remaining unreacted, obtained in production step 1-(11) was confirmed. Therefore, the above procedure was repeated to give the following compound (0.0080 g, 93%).

$R_f$ 0.60 (Hex:AcOEt=4:1); $^1$H NMR (400 MHz, CDCl$_3$) δ 8.12-8.02 (2H, m), 7.60-7.51 (1H, m), 7.49-7.40 (2H, m), 7.15 (1H, J=15.4, 9.8 Hz), 6.12-5.97 (2H, m), 5.74 (1H, d, J=15.4 Hz), 5.64 (1H, q, J=6.3 Hz), 5.14-5.02 (1H, m), 4.17 (2H, q, J=7.1 Hz), 2.85-2.76 (1H, m), 2.42-2.34 (1H, m), 2.28-2.18 (1H, m), 2.01-1.90 (1H, m), 1.88-1.75 (2H, m), 1.71-1.56 (6H, m), 1.55 (3H, s), 1.27 (3H, t, J=7.1 Hz), 1.07 (3H, s), 0.97 (3H, d, J=6.8 Hz), 0.84-0.76 (1H, m), 0.74-0.67 (1H, m), 0.41-0.33 (1H, m).

[Chemical formula 21]

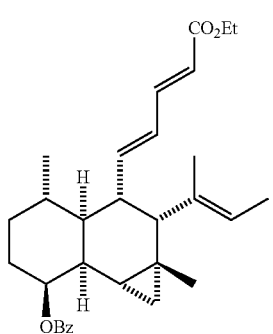

Production Step 1-(13)

LiOH.H$_2$O (0.0104 g, 0.248 mmol) was added to a solution (0.5 ml) of the compound (0.0080 g, 0.0168 mmol) obtained in production step 1-(12) in EtOH/H$_2$O (4/1) under an argon atmosphere, and the mixture was stirred at room temperature for one day. After the completion of the reaction, a saturated aqueous NH$_4$Cl solution was added to the reaction solution, followed by separation. The aqueous layer was extracted with AcOEt, and the collected oil layer was dried over Na$_2$SO$_4$. The dried oil layer was filtered, and the solvent was then removed under the reduced pressure. The residue was purified by column chromatography on silica gel (Hex:AcOEt=1:3) to give the title compound: (2E,4E)-5-{(1aR,2R,3S,3aS,4S,7S,7aS,7bR)-2-[(E)-but-2-en-2-yl]-decahydro-7-hydroxy-1a,4-dimethyl-1H-cyclopropa[a]naphthalen-3-yl}penta-2,4-dienoic acid (0.0058 g, 100%).

$R_f$ 0.44 (Hex:AcOEt=1:10); $^1$H NMR (600 MHz, CDCl$_3$) δ 7.26 (1H, dd, J=15.4, 7.7 Hz), 6.12-6.08 (2H, m), 5.74 (1H, d, J=15.4 Hz), 5.66 (1H, qt, J=6.7, 1.3 Hz), 3.74 (1H, ddd, J=12.0, 4.6, 4.6 Hz), 2.81-2.76 (1H, m), 2.35 (1H, d, J=6.1 Hz), 2.03-1.97 (1H, m), 1.80-1.69 (2H, m), 1.69-1.57 (4H, m), 1.55 (3H, s), 1.52-1.43 (1H, m), 1.19 (1H, ddd, J=10.8, 3.6, 3.6 Hz), 1.12-1.01 (4H, m), 0.93 (3H, d, J=6.7 Hz), 0.74 (1H, dd, J=9.0, 4.6 Hz), 0.63-0.57 (1H, m), 0.35 (1H, dd, J=4.6, 4.6 Hz); $^{13}$C NMR (150 MHz, CDCl$_3$) δ 171.6, 147.6, 147.5, 134.2, 128.3, 120.3, 118.0, 73.3, 47.0, 44.9, 39.8, 38.9, 33.4, 30.3, 28.8, 27.4, 20.5, 18.7, 16.2, 15.8, 15.6, 13.4; FAB-MS: [M+Na]$^+$ calculated for C$_{22}$H$_{32}$O$_3$Na: 367.2249. Found: 367.2240.

[Chemical formula 22]

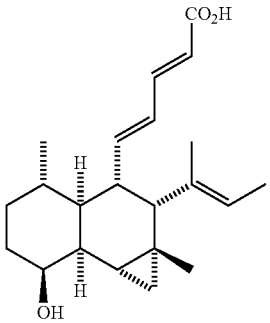

Example 2

Synthesis of (2E,4E)-5-{(1S,4S,4aS,5S,6R,7S,8aR)-6-[(E)-but-2-en-2-yl]-decahydro-1-hydroxy-4,7-dimethylnaphthalen-5-yl}penta-2,4-dienoic acid Production Step 2-(1)

[Ir(cod)pyr(PCy$_3$)]PF$_6$ (Crabtree's catalyst) (0.0084 g, 0.0104 mmol) was dissolved in degassed (CH$_2$Cl)$_2$ (0.4 ml) under an argon atmosphere. A solution of starting compound 1 (0.0330 g, 0.0520 mmol) dissolved in degassed (CH$_2$Cl)$_2$ (2.5 ml) was added to the solution. An H$_2$ gas (1 atm) was sealed. The temperature was then raised to 60° C., followed by stirring for 2 hr. After the completion of the reaction, a saturated aqueous NH$_4$Cl solution was added to the reaction solution, followed by separation. The aqueous layer was extracted with CH$_2$Cl$_2$, and the collected oil layer was dried over Na$_2$SO$_4$. The dried oil layer was filtered, and the solvent was then removed under the reduced pressure. The residue was purified by column chromatography on silica gel (Hex: AcOEt=20:1) to give the following compound (0.0279 g, 84%).

R$_f$ 0.35 (Benzen:AcOEt=100:1, 2 times eluent); $^1$H NMR (400 MHz, CDCl$_3$) δ 7.75-7.66 (4H, m), 7.49-7.33 (6H, m), 4.09 (1H, dd, J=10.2, 9.0 Hz), 3.84-3.76 (1H, m), 3.74-3.66 (1H, m), 3.58-3.49 (2H, m), 3.41 (1H, dd, J=10.5, 2.7 Hz), 2.25-2.18 (1H, br), 1.76-1.42 (8H, m), 1.17-0.86 (36H, m), 0.77 (3H, d, J=6.1 Hz).

R$_f$ 0.41 (Hex:AcOEt=20:1); $^1$H NMR (400 MHz, CDCl$_3$) δ 7.70-7.63 (4H, m), 7.44-7.32 (6H, m), 4.12 (1H, dd, J=9.8, 3.4 Hz), 3.85-3.70 (2H, m), 2.31-2.18 (2H, m), 2.14-2.05 (1H, m), 1.90 (1H, d, J=2.4 Hz), 1.78-1.68 (3H, m), 1.66-1.47 (1H, m), 1.09-1.00 (35H, m), 0.99 (3H, d, J=6.3 Hz), 0.90 (3H, d, J=6.3 Hz).

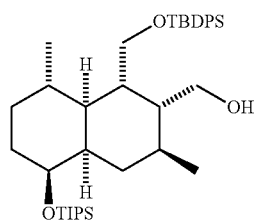

[Chemical formula 23]

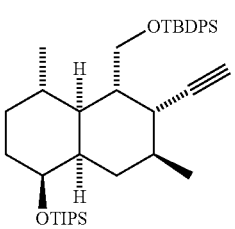

[Chemical formula 26]

Production Step 2-(2)

The following compound (0.0611 g, 95%) was obtained from the compound (0.0613 g, 0.0962 mmol) obtained in production step 2-(1) by carrying out a reaction under the same conditions as in production step 1-(2).

R$_f$ 0.67 (Hex:AcOEt=4:1); $^1$H NMR (400 MHz, CDCl$_3$) δ 9.70 (1H, d, J=2.7 Hz), 7.68-7.59 (4H, m), 7.46-7.34 (6H, m), 3.86 (1H, dd, J=10.2, 8.3 Hz), 3.68-3.60 (1H, m), 3.54 (1H, dd, J=10.2, 6.3 Hz), 2.51-2.41 (1H, m), 2.09 (1H, ddd, J=11.7, 3.4, 3.4 Hz), 1.99-1.84 (2H, m), 1.78 (1H, ddd, J=17.3, 3.7, 3.7 Hz), 1.74-1.49 (4H, m), 1.15-0.98 (33H, m), 0.96 (3H, d, J=6.1 Hz), 0.84 (3H, d, J=6.1 Hz).

Production Step 2-(5)

The following compound (0.0393 g, 99%) was obtained from the compound (0.0323 g, 0.0512 mmol) obtained in production step 2-(4) by carrying out a reaction under the same conditions as in production step 1-(5).

R$_f$ 0.62 (Hex:AcOEt=20:1); $^1$H NMR (400 MHz, CDCl$_3$) δ 7.67-7.56 (4H, m), 7.46-7.33 (6H, m), 5.66 (1H, s), 3.76 (1H, ddd, J=10.7, 5.4, 5.4 Hz), 3.63 (1H, dd, J=9.8, 9.8 Hz), 3.53 (1H, dd, J=9.8, 3.9 Hz), 2.13-1.97 (3H, m), 1.83-1.67 (3H, m), 1.60 (3H, s), 1.13-0.95 (36H, m), 0.87 (3H, d, J=5.6 Hz), 0.79 (3H, d, J=6.1 Hz).

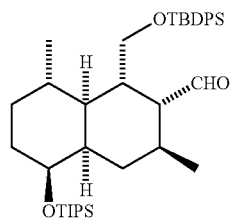

[Chemical formula 24]

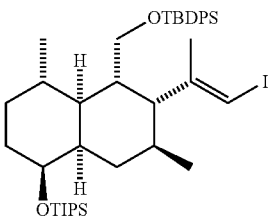

[Chemical formula 27]

Production Step 2-(3)

The following compound (0.0572 g, 79%) was obtained from the compound (0.0578 g, 0.0910 mmol) obtained in production step 2-(2) by carrying out a reaction under the same conditions as in production step 1-(3).

R$_f$ 0.64 (Hex:AcOEt=10:1); $^1$H NMR (400 MHz, CDCl$_3$) δ 7.69-7.62 (4H, m), 7.47-7.36 (6H, m), 6.18 (1H, d, J=8.8 Hz), 3.77-3.66 (3H, m), 2.28-2.19 (2H, m), 2.10-2.00 (1H, m), 1.79-1.66 (3H, m), 1.64-1.48 (1H, m), 1.09-0.98 (35H, m), 0.91 (3H, d, J=6.1 Hz), 0.81 (3H, d, J=6.3 Hz).

Production Step 2-(6)

The following compound (0.0307 g, 91%) was obtained from the compound (0.0393 g, 0.0508 mmol) obtained in production step 2-(5) by carrying out a reaction under the same conditions as in production step 1-(6).

R$_f$ 0.44 (Hex:AcOEt=30:1); $^1$H NMR (400 MHz, CDCl$_3$) δ 7.68-7.57 (4H, m), 7.45-7.30 (6H, m), 4.92 (1H, q, J=6.6 Hz), 3.82-3.73 (1H, m), 3.65 (1H, dd, J=10.0, 10.0 Hz), 3.57 (1H, dd, J=10.0, 4.4 Hz), 2.18-2.07 (1H, m), 2.06-1.96 (1H, m), 1.82-1.66 (6H, m), 1.66-1.55 (2H, m), 1.40 (3H, d, J=6.6 Hz), 1.37 (3H, s), 1.16-0.95 (32H, m), 0.88 (3H, d, J=4.9 Hz), 0.76 (3H, d, J=6.1 Hz).

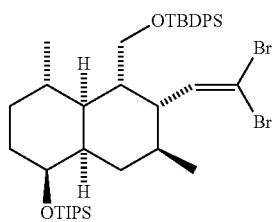

[Chemical formula 25]

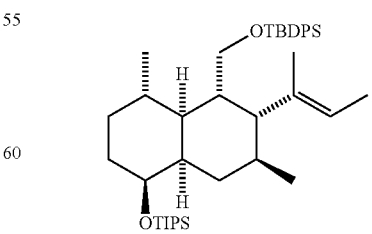

[Chemical formula 28]

Production Step 2-(4)

The following compound (0.0439 g, 96%) was obtained from the compound (0.0572 g, 0.0723 mmol) obtained in production step 2-(3) by carrying out a reaction under the same conditions as in production step 1-(4).

Production Step 2-(7)

The following compound (0.0154 g, 99%) was obtained from the compound (0.0387 g, 0.0585 mmol) obtained in production step 2-(6) by carrying out a reaction under the same conditions as in production step 1-(7).

R$_f$ 0.14 (Hex:AcOEt=1:1)

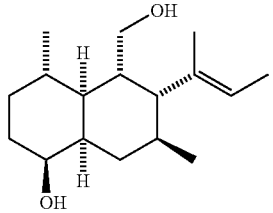

[Chemical formula 29]

Production Step 2-(8)

The following compound (0.0166 g, 75%) was obtained from the compound (0.0154 g, 0.0578 mmol) obtained in production step 2-(7) by carrying out a reaction under the same conditions as in production step 1-(8).

R$_f$ 0.79 (Hex:AcOEt=1:1); $^1$H NMR (400 MHz, CDCl$_3$) δ 5.10 (1H, q, J=6.8 Hz), 3.75-3.66 (1H, m), 3.62-3.53 (2H, m), 2.20-2.07 (1H, m), 1.97-1.88 (1H, m), 1.86-1.56 (14H, m), 1.18-1.00 (2H, m), 0.99-0.85 (12H, m), 0.83 (3H, d, J=6.3 Hz), 0.08-0.00 (6H, m).

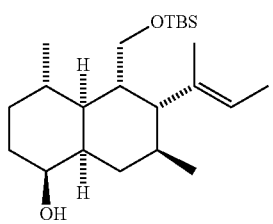

[Chemical formula 30]

Production Step 2-(9)

The following compound (0.0216 g, quant.) was obtained from the compound (0.0166 g, 0.0436 mmol) obtained in production step 2-(8) by carrying out a reaction under the same conditions as in production step 1-(9).

R$_f$ 0.77 (Hex:AcOEt=4:1); $^1$H NMR (400 MHz, CDCl$_3$) δ 8.11-8.00 (2H, m), 7.60-7.50 (1H, m), 7.49-7.40 (2H, m), 5.13-5.01 (2H, m), 3.60-3.51 (2H, m), 2.41-2.30 (1H, m), 1.98-1.90 (1H, m), 1.89-1.47 (14H, m), 1.34-1.16 (2H, m), 0.93-0.85 (12H, m), 0.83 (3H, d, J=6.1 Hz), 0.04--0.04 (6H, m).

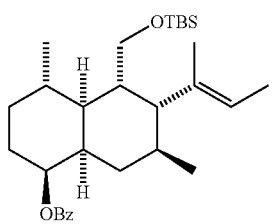

[Chemical formula 31]

Production Step 2-(10)

The following compound (0.0167 g, quant.) was obtained from the compound (0.0216 g, 0.0435 mmol) obtained in production step 2-(9) by carrying out a reaction under the same conditions as in production step 1-(10).

R$_f$ 0.24 (Hex:AcOEt=4:1); $^1$H NMR (400 MHz, CDCl$_3$) δ 8.07-8.00 (2H, m), 7.60-7.51 (1H, m), 7.48-7.40 (2H, m), 5.22 (1H, q, J=6.1 Hz), 5.10-5.02 (1H, m), 3.86-3.78 (1H, m), 3.52-3.42 (1H, m), 2.26-2.16 (1H, m), 2.13-2.06 (1H, m), 1.90-1.68 (8H, m), 1.67-1.61 (6H, m), 1.41-1.16 (2H, m), 0.93 (3H, d, J=6.3 Hz), 0.88 (3H, d, J=5.9 Hz).

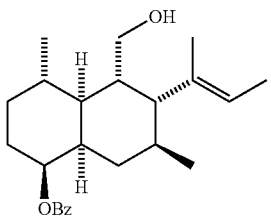

[Chemical formula 32]

Production Step 2-(11)

The following compound (0.0151 g, 91%) was obtained from the compound (0.0167 g, 0.0451 mmol) obtained in production step 2-(10) by carrying out a reaction under the same conditions as in production step 1-(11).

R$_f$ 0.56 (Hex:AcOEt=4:1); $^1$H NMR (400 MHz, CDCl$_3$) δ 9.94 (1H, d, J=2.2 Hz), 8.06-8.00 (2H, m), 7.58-7.50 (1H, m), 7.47-7.40 (2H, m), 5.34 (1H, q, J=5.1 Hz), 5.06 (1H, ddd, J=12.0, 4.9, 4.9 Hz), 2.59-2.55 (1H, m), 2.35-2.26 (1H, m), 2.05-1.71 (8H, m), 1.67-1.58 (6H, m), 1.46-1.16 (2H, m), 0.94 (3H, d, J=5.9 Hz), 0.91 (3H, d, J=5.6 Hz).

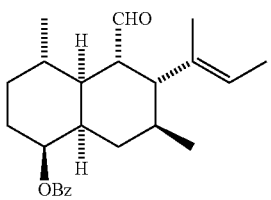

[Chemical formula 33]

Production Step 2-(12)

The following compound (0.0186 g, 98%) was obtained from the compound (0.0151 g, 0.0410 mmol) obtained in production step 2-(11) by carrying out a reaction under the same conditions as in production step 1-(12). When the compound obtained in production step 2-(11) was used, unlike the case where the compound obtained in production step 1-(11), the compound obtained in production step 2-(11) was entirely consumed in a single reaction without repeating the reaction procedure.

R$_f$ 0.56 (Hex:AcOEt=4:1); $^1$H NMR (400 MHz, CDCl$_3$) δ 8.06-8.00 (2H, m), 7.60-7.51 (1H, m), 7.48-7.41 (2H, m), 7.31-7.19 (1H, m), 6.43 (1H, dd, J=14.9, 9.1 Hz), 6.07 (1H, dd, J=14.9, 9.1 Hz), 5.77 (1H, d, J=15.1 Hz), 5.15 (1H, q, J=6.3 Hz), 5.00 (1H, ddd, J=10.7, 5.4, 5.4 Hz), 4.24-4.15 (2H, m), 2.64-2.58 (1H, m), 2.44-2.38 (1H, m), 1.95-1.75 (6H, m), 1.63-1.48 (5H, m), 1.45 (3H, s), 1.29 (3H, t, J=7.1 Hz), 1.25-1.03 (2H, m), 0.95 (3H, d, J=6.3 Hz), 0.85 (3H, d, J=6.1 Hz).

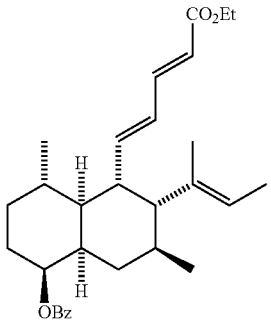

[Chemical formula 34]

Production step 2-(13)

The title compound: (2E,4E)-5-{(1S,4S,4aS,5S,6R,7S,8aR)-6-[(E)-but-2-en-2-yl]-decahydro-1-hydroxy-4,7-dimethylnaphthalen-5-yl}penta-2,4-dienoic acid (0.0125 g, 94%) was obtained from the compound (0.0186 g, 0.0400 mmol) obtained in production step 2-(12) by carrying out a reaction under the same conditions as in production step 1-(13). In this case, purification was carried out by column chromatography on silica gel (Hex:AcOEt=1:1).

$R_f$ 0.14 (Hex:AcOEt=1:1); $^1$H NMR (600 MHz, CD$_3$OD) δ 7.23 (1H, dd, J=15.1, 11.0 Hz), 6.54 (1H, dd, J=14.8, 9.5 Hz), 6.09 (1H, dd, J=14.8, 11.0 Hz), 5.76 (1H, d, J=15.1 Hz), 5.18 (1H, q, J=6.7 Hz), 3.58 (1H, ddd, J=10.2, 5.1, 5.1 Hz), 2.68-2.58 (1H, m), 2.19-2.12 (1H, m), 1.96-1.69 (6H, m), 1.67-1.53 (5H, m), 1.49 (3H, s), 1.30-1.04 (2H, m), 0.91 (3H, d, J=6.4 Hz), 0.84 (3H, d, J=6.1 Hz); $^{13}$C NMR (150 MHz, CD$_3$OD) δ 170.9, 148.5, 147.0, 137.8, 129.8, 121.5, 120.5, 73.8, 53.1, 51.5, 46.5, 39.3, 35.1, 30.4, 30.2, 30.0, 28.8, 21.3, 19.7, 15.9, 13.3; FAB-MS: [M+H]$^+$ calculated for C$_{21}$H$_{33}$O$_3$: 333.2430. Found: 333.2435.

[Chemical formula 35]

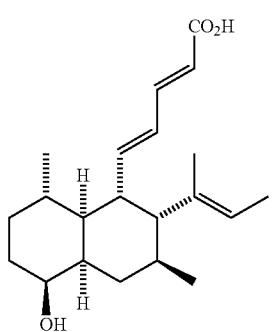

Example 3

Synthesis of (2E,4E)-5-{(1S,4S,4aS,5S,6R,7S,8aR)-6-[(Z)-but-2-en-2-yl]-decahydro-1-hydroxy-4,7-dimethylnaphthalen-5-yl}penta-2,4-dienoic acid (first synthesis method)

Production Step 3-(1)

A hexane solution (0.1439 ml, 1.63 M) of n-BuLi was added to a solution (0.5 ml) of iPr$_2$NH (0.0365 ml, 0.260 mmol) in THF at 0° C. under an argon atmosphere, and the mixture was stirred for 10 min. The mixture was cooled to −78° C. AcOMe (0.0207 ml, 0.261 mmol) was then added to the cooled solution, and the mixture was stirred for 10 min. A solution (1.2 ml) of the compound (0.0331 g, 0.0521 mmol) obtained in production step 2-(2) in THF was added to thereto, and the mixture was stirred. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=10:1) to give the following compound (0.0365 g, 99%).

$R_f$ 0.40 (Hex:AcOEt=4:1); $^1$H NMR (400 MHz, CDCl$_3$) δ 7.72-7.60 (4H, m), 7.48-7.31 (6H, m), 4.22-4.10 (1H, m), 4.03-3.94 (1H, m), 3.73-3.66 (3H, m), 3.62-3.54 (1H, m), 3.48-3.40 (1H, m), 2.78-2.62 (1H, m), 2.55-2.39 (1H, m), 2.07-1.94 (1H, m), 1.84-1.34 (9H, m), 1.17-0.85 (35H, m), 0.72 (3H, d, J=6.1 Hz).

[Chemical formula 36]

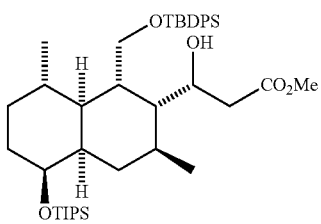

Production Step 3-(2)

A Dess-Martin reagent (0.0436 g, 0.103 mmol) was added to a solution (2 ml) of the compound (0.0365 g, 0.0515 mmol) obtained in production step 3-(1) in CH$_2$Cl$_2$ under an argon atmosphere, and the mixture was stirred at room temperature. After the completion of the reaction, the reaction solution was diluted with Et$_2$O, and a saturated aqueous Na$_2$S$_2$O$_3$ solution and a saturated aqueous NaHCO$_3$ solution were added to the diluted solution, followed by separation. The aqueous layer was extracted with Et$_2$O, and the collected oil layer was dried over MgSO$_4$. The dried oil layer was filtered, and the solvent was then removed under the reduced pressure. The residue was purified by column chromatography on silica gel (Hex:AcOEt=30:1) to give the following compound (0.0310 g, 85%).

$R_f$ 0.27 (Hex:AcOEt=10:1); $^1$H NMR (400 MHz, CDCl$_3$) δ 7.66-7.57 (4H, m), 7.46-7.31 (6H, m), 3.73-3.67 (1H, m), 3.66 (3H, s), 3.60 (1H, dd, J=10.5, 8.3 Hz), 3.48 (1H, dd, J=10.5, 5.6 Hz), 3.36 (1H, d, J=14.9 Hz), 3.17 (1H, d, J=14.9 Hz), 2.51 (1H, dd, J=11.5, 4.1 Hz), 2.35-2.24 (1H, m), 1.96-1.49 (8H, m), 1.12-0.95 (32H, m), 0.92 (3H, d, J=5.9 Hz), 0.83 (3H, d, J=6.1 Hz).

[Chemical formula 37]

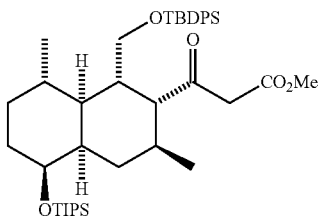

Production Step 3-(3)

Et$_3$N (0.0611 ml, 0.438 mmol) was added to a solution (1.5 ml) of the compound (0.0310 g, 0.0438 mmol) obtained in production step 3-(2) in HMPA at 0° C. under an argon atmosphere, and the mixture was stirred for 2 hr. ClP(O)(OPh)$_2$ (0.0907 ml, 0.260 mmol) and DMAP (0.0005 g, 0.00409 mmol) were added to the reaction solution, and the mixture was stirred at room temperature. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=10:1) to give the following compound (0.0403 g, 98%).

$R_f$ 0.51 (Hex:AcOEt=4:1); $^1$H NMR (400 MHz, CDCl$_3$) δ 7.65-7.54 (4H, m), 7.44-7.26 (6H, m), 7.23-7.16 (2H, m), 7.16-7.05 (4H, m), 7.01-6.94 (2H, m), 6.91-6.84 (2H, m), 5.90 (1H, s), 3.77-3.55 (6H, m), 2.26-2.17 (1H, m), 1.97-1.88 (1H, m), 1.86-1.69 (3H, m), 1.64-1.51 (3H, m), 1.15-0.97 (34H, m), 0.94 (3H, d, J=5.4 Hz), 0.65 (3H, d, J=5.9 Hz).

[Chemical formula 38]

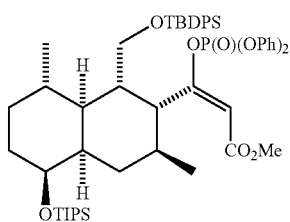

Production Step 3-(4)

The compound (0.111 g, 0.118 mmol) obtained in production step 3-(3) and Fe(acac)$_3$ (0.208 g, 0.591 mmol) were mixed together, and the mixture was subjected to azeotropic distillation with toluene under an argon atmosphere. NMP (4 ml) was then added to prepare a solution. An empty eggplant flask was subjected to azeotropic distillation with toluene under an argon atmosphere. NMP (1 ml) was added thereto, and the mixture was cooled to 0° C. A THF solution (2.37 ml, 3.0 M) of MeMgCl was added to the cooled mixture. The solution prepared above was gradually added dropwise to the mixture, and the mixture was stirred. After the completion of the reaction, a saturated aqueous NH$_4$Cl solution was added to the reaction solution, followed by separation. The aqueous layer was extracted with Et$_2$O, and the collected oil layer was dried over Na$_2$SO$_4$. The dried oil layer was filtered, and the solvent was then removed under the reduced pressure. The residue was purified by column chromatography on silica gel (Hex:AcOEt=50:1) to give the following compound (0.0763 g, 91%).

$R_f$ 0.58 (Hex:AcOEt=10:1); $^1$H NMR (400 MHz, CDCl$_3$) δ 7.68-7.57 (4H, m), 7.45-7.30 (6H, m), 5.60 (1H, s), 3.78-3.59 (6H, m), 2.21-2.14 (1H, m), 2.06-1.97 (1H, m), 1.89-1.71 (2H, m), 1.65 (3H, s), 1.63-1.53 (4H, m), 1.19-1.10 (34H, m), 0.96 (3H, d, J=6.1 Hz), 0.76 (3H, d, J=6.1 Hz).

[Chemical formula 39]

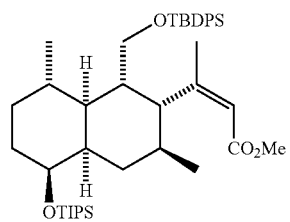

Production Step 3-(5)

A hexane solution (0.414 ml, 0.98 M) of DIBAL was added to a solution (3 ml) of the compound (0.0763 g, 0.108 mmol) obtained in production step 2-(4) in CH$_2$Cl$_2$ at −78° C. under an argon atmosphere, and the mixture was stirred. After the completion of the reaction, MeOH was added thereto until foams were no longer produced. The temperature of the solution was then raised to room temperature before a saturated aqueous potassium sodium tartarate solution was added thereto. The mixture was stirred for 30 min, followed by separation. The aqueous layer was extracted with CH$_2$Cl$_2$, and the collected oil layer was dried over Na$_2$SO$_4$. The dried oil layer was filtered, and the solvent was then removed under the reduced pressure. The residue was purified by column chromatography on silica gel (Hex:AcOEt=10:1) to give the following compound (0.0720 g, 98%).

$R_f$ 0.17 (Hex:AcOEt=10:1); $^1$H NMR (400 MHz, CDCl$_3$) δ 7.67-7.56 (4H, m), 7.46-7.30 (6H, m), 5.36-5.28 (1H, m), 4.22-4.12 (1H, m), 4.04-3.95 (1H, m), 3.80-3.68 (2H, m), 3.64 (1H, dd, J=9.5, 5.1 Hz), 2.39-2.30 (1H, m), 2.11-2.02 (1H, m), 1.92-1.66 (4H, m), 1.66-1.50 (4H, m), 1.47 (3H, s), 1.16-0.96 (32H, m), 0.87 (3H, d, J=5.1 Hz), 0.76 (3H, d, J=6.1 Hz).

[Chemical formula 40]

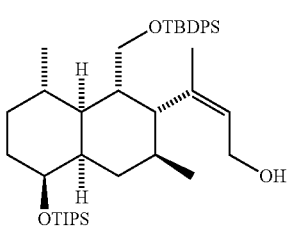

Production Step 3-(6)

Pyridine (0.0258 ml, 0.319 mmol) and PBr$_3$ (0.111 ml, 1.063 mmol) were added to a solution (3 ml) of the compound (0.0720 g, 0.106 mmol) obtained in production step 3-(5) in Et$_2$O at 0° C. under an argon atmosphere, and the mixture was stirred. After the completion of the reaction, the reaction solution as such was crudely produced by column chromatography on silica gel (Et$_2$O) to obtain the following crude compound. The crude product as such was used in the next reaction.

$R_f$ 0.64 (Hex:AcOEt=10:1).

[Chemical formula 41]

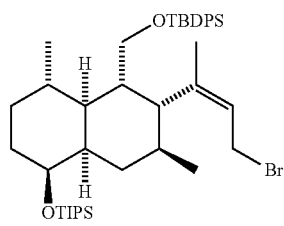

Production Step 3-(7)

LiAlH$_4$ (0.0274 g, 0.578 mmol) was added to a solution (3 ml) of the crude compound obtained in production step 3-(6) in Et$_2$O under an argon atmosphere in an ice bath, and the mixture was stirred. After the completion of the reaction, a saturated aqueous Na$_2$SO$_4$ solution was added to the reaction solution under foams were no longer produced, and the precipitated solid was collected through Celite. The solvent was removed under the reduced pressure, and the residue was purified by column chromatography on silica gel (Hex:AcOEt=100:1) to give the following compound (0.0513 g, 73%) (two steps).

$R_f$ 0.22 (Hex:AcOEt=30:1); $^1$H NMR (400 MHz, CDCl$_3$) δ 7.68-7.59 (4H, m), 7.44-7.30 (6H, m), 5.19-5.11 (1H, m), 3.82-3.70 (2H, m), 3.66 (1H, dd, J=9.8, 5.1 Hz), 2.40-2.33 (1H, m), 2.14-1.99 (2H, m), 1.84-1.70 (5H, m), 1.66-1.57 (2H, m), 1.55 (3H, d, J=6.1 Hz), 1.39 (3H, s), 1.14-0.98 (32H, m), 0.89 (3H, d, J=5.6 Hz), 0.75 (3H, d, J=6.1 Hz).

[Chemical formula 42]

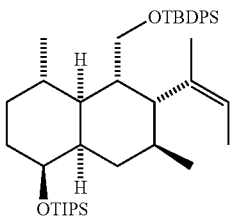

Production Step 3-(8)

The following compound (0.0190 g, 92%) was obtained from the compound (0.0513 g, 0.0776 mmol) obtained in production step 3-(7) by carrying out a reaction under the same conditions as in production step 1-(7). In this case, purification was carried out by column chromatography on silica gel (Hex:AcOEt=1:1).

$R_f$ 0.21 (Hex:AcOEt=1:1); $^1$H NMR (400 MHz, CD$_3$OD) δ 4.84 (1H, q, J=6.8 Hz), 3.20-3.05 (3H, m), 2.01-1.90 (1H, m), 1.65-1.54 (1H, m), 1.54-1.42 (1H, m), 1.38-1.18 (7H, m), 1.15 (3H, s), 1.11 (3H, dd, J=6.8, 1.0 Hz), 0.70-0.50 (2H, m), 0.41 (3H, d, J=6.1 Hz), 0.31 (3H, d, J=5.9 Hz).

[Chemical formula 43]

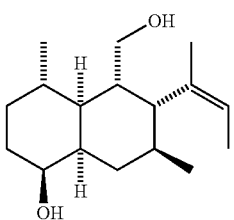

Production Step 3-(9)

The following compound (0.0262 g, 97%) was obtained from the compound (0.0190 g, 0.0713 mmol) obtained in production step 3-(8) by carrying out a reaction under the same conditions as in production step 1-(8).

$R_f$ 0.80 (Hex:AcOEt=1:1); $^1$H NMR (400 MHz, CDCl$_3$) 5.31 (1H, q, J=6.8 Hz), 3.73-3.53 (3H, m), 2.45-2.36 (1H, m), 2.15-2.05 (1H, m), 1.98-1.88 (1H, m), 1.84-1.71 (2H, m), 1.71-1.48 (9H, m), 1.15-1.01 (2H, m), 0.90-0.84 (12H, m), 0.80 (3H, d, J=6.1 Hz), 0.03-0.00 (6H, m).

[Chemical formula 44]

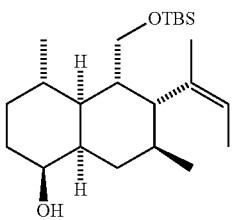

Production Step 3-(10)

The following compound (0.0066 g, quant.) was obtained from the compound (0.0052 g, 0.0137 mmol) obtained in production step 3-(9) by carrying out a reaction under the same conditions as in production step 1-(9).

$R_f$ 0.70 (Hex:AcOEt=4:1); $^1$H NMR (400 MHz, CDCl$_3$) δ 8.10-8.01 (2H, m), 7.61-7.50 (1H, m), 7.50-7.40 (2H, m), 5.32 (1H, q, J=5.9 Hz), 5.12-5.00 (1H, m), 3.70-3.49 (2H, m), 2.52-2.28 (2H, m), 2.02-1.54 (12H, m), 1.40-1.13 (4H, m), 1.01-0.83 (12H, m), 0.82 (3H, d, J=6.1 Hz), 0.09-0.00 (6H, m).

[Chemical formula 45]

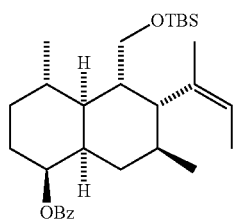

Production Step 3-(11)

The following compound (0.0055 g, quant.) was obtained from the compound (0.0066 g, 0.0133 mmol) obtained in production step 3-(10) by carrying out a reaction under the same conditions as in production step 1-(10). In this case, purification was carried out by column chromatography on silica gel (Hex:AcOEt=8:1).

$R_f$ 0.30 (Hex:AcOEt=4:1); $^1$H NMR (400 MHz, CDCl$_3$) δ 8.12-8.02 (2H, m), 7.63-7.51 (1H, m), 7.51-7.40 (2H, m), 5.36 (1H, q, J=6.9 Hz), 5.07 (1H, ddd, J=10.7, 5.4, 5.4 Hz), 3.77 (1H, dd, J=10.2, 4.9 Hz), 3.65 (1H, dd, J=10.2, 10.2 Hz), 2.54-2.41 (1H, m), 2.39-2.26 (1H, m), 2.14-1.46 (12H, m), 1.42-1.14 (4H, m), 0.96 (3H, d, J=6.1 Hz), 0.84 (3H, d, J=5.9 Hz).

[Chemical formula 46]

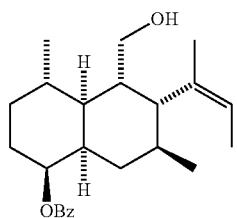

Production Step 3-(12)

The following compound (0.0045 g, 82%) was obtained from the compound (0.0055 g, 0.0148 mmol) obtained in production step 3-(11) by carrying out a reaction under the same conditions as in production step 1-(11).

$R_f$ 0.52 (Hex:AcOEt=4:1); $^1$H NMR (400 MHz, CDCl$_3$) δ 10.0 (1H, d, J=2.2 Hz), 8.09-8.00 (2H, m), 7.60-7.51 (1H, m), 7.49-7.40 (2H, m), 5.42 (1H, q, J=5.9 Hz), 5.08 (1H, ddd, J=11.5, 4.9, 4.9 Hz), 2.68-2.55 (2H, m), 2.47-2.38 (1H, m), 1.98-1.50 (13H, m), 1.47-1.16 (2H, m), 0.94 (3H, d, J=6.3 Hz), 0.89 (3H, d, J=6.1 Hz).

[Chemical formula 47]

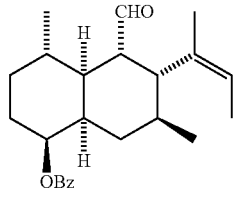

Production Step 3-(13)

The following compound (0.0051 g, 89%) was obtained from the compound (0.0045 g, 0.0122 mmol) obtained in production step 3-(12) by carrying out a reaction under the same conditions as in production step 1-(12).

$R_f$ 0.52 (Hex:AcOEt=4:1); $^1$H NMR (400 MHz, CDCl$_3$) δ 8.11-8.00 (2H, m), 7.63-7.51 (1H, m), 7.50-7.40 (2H, m), 7.34-7.18 (1H, m), 6.54 (1H, dd, J=14.6, 10.0 Hz), 6.10 (1H, dd, J=14.6, 11.0 Hz), 5.78 (1H, d, J=15.4 Hz), 5.27 (1H, q, J=6.1 Hz), 5.07-4.95 (1H, m), 4.27-4.11 (2H, m), 2.66-2.35 (3H, m), 2.02-1.66 (7H, m), 1.60 (3H, d, J=6.1 Hz), 1.50 (3H, s), 1.29 (3H, t, J=7.1 Hz), 1.23-1.09 (2H, m), 0.98 (3H, d, J=6.3 Hz), 0.83 (3H, d, J=5.6 Hz).

[Chemical formula 48]

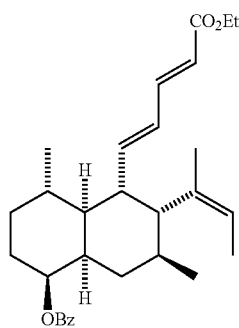

Production Step 3-(14)

The title compound: (2E,4E)-5-{(1S,4S,4aS,5S,6R,7S,8aR)-6-[(Z)-but-2-en-2-yl]-decahydro-1-hydroxy-4,7-dimethylnaphthalen-5-yl}penta-2,4-dienoic acid (0.0032 g, 89%) was obtained from the compound (0.0051 g, 0.0110 mmol) obtained in production step 3-(13) by carrying out a reaction under the same conditions as in production step 1-(13). In this case, purification was carried out by column chromatography on silica gel (Hex:AcOEt=2:1).

$R_f$ 0.29 (Hex:AcOEt=1:1); $^1$H NMR (400 MHz, CDCl$_3$) δ 7.35 (1H, dd, J=15.4, 11.0 Hz), 6.63 (1H, dd, J=14.9, 9.8 Hz), 6.13 (1H, dd, J=14.9, 11.0 Hz), 5.79 (1H, d, J=15.4 Hz), 5.27 (1H, qd, J=6.8, 1.0 Hz), 3.67 (1H, ddd, J=11.5, 4.9, 4.9 Hz), 2.58-2.46 (2H, m), 2.24-2.14 (1H, m), 1.93-1.62 (7H, m), 1.59 (3H, dd, J=6.8, 0.7 Hz), 1.51 (3H, s), 1.24-1.00 (2H, m), 0.94 (3H, d, J=6.3 Hz), 0.83 (3H, d, J=6.1 Hz); FAB-MS: [M+Na]$^+$ calculated for C$_{21}$H$_{32}$O$_3$Na: 355.2249. Found: 355.2249.

[Chemical formula 49]

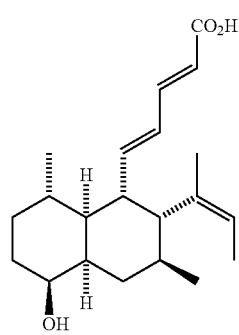

In Example 4, $^1$H-NMR was measured with spectrometer JEOL AL 400. Tetramethylsilane was used as an internal standard.

For thin-layer chromatography, TLC 60E-254 (manufactured by Merck Ltd.) was used, and UV lamp and phosphomolybdic acid were used for detection.

Silica Gel 60N (spherical, neutral) 63-210 μm (manufactured by KANTO CHEMICAL CO., INC.) and Silica Gel 60N (spherical, neutral) 40-50 μm (manufactured by KANTO CHEMICAL CO., INC.) were used for chromatography on silica gel.

MK8383 obtained by culturing MK8383 producing microorganism *Phoma* sp. according to the method described in Japanese Patent Application Laid-Open No. 126211/1995 and WO 99/11596 and purifying the culture solution was used.

Example 4

Synthesis of (2E,4E)-5-{(1S,4S,4aS,5S,6R,7S,8aR)-6-[(Z)-but-2-en-2-yl]-decahydro-1-hydroxy-4,7-dimethylnaphthalen-5-yl}penta-2,4-dienoic acid (second synthesis method)

Production Step 4-(1)

An Et$_2$O solution (0.0832 ml, 2.0 M) of TMSCHN$_2$ was added to a solution (1.8 ml) of MK8383 (0.0423 g, 0.128 mmol) in benzene/MeOH (5/1) under an argon atmosphere, and the mixture was stirred at room temperature. After the completion of the reaction, a small amount of glacial acetic acid was added to the reaction solution. When the light yellow of the reaction solution disappeared, the solvent was removed under the reduced pressure. The residue was purified by column chromatography on silica gel (Hex:AcOEt=7:1) to give the following compound (0.0440 g, quant.).

$R_f$ 0.65 (Hex:AcOEt=1:1); $^1$H NMR (400 MHz, CDCl$_3$) δ 7.26-7.19 (1H, m), 6.21-6.09 (2H, m), 5.78 (1H, d, J=15.4 Hz), 5.62 (1H, s), 5.37 (1H, q, J=5.6 Hz), 3.76-3.69 (4H, m), 3.38-3.22 (1H, m), 2.99-2.78 (1H, m), 2.68-2.51 (1H, m), 1.76-1.57 (15H, m), 0.96 (3H, d, J=6.8 Hz).

[Chemical formula 50]

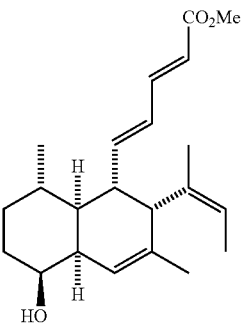

Production Step 4-(2)

2,6-Lutidine (0.0298 ml, 0.256 mmol) and TIPSOTf (0.0549 ml, 0.204 mmol) were added in that order to a solution (1.3 ml) of the compound (0.0440 g, 0.128 mmol) obtained in production step 4-(1) in CH$_2$Cl$_2$ under an argon atmosphere, and the mixture was stirred at room temperature. After the completion of the reaction, a saturated aqueous NH$_4$Cl solution (3 ml) was added to the reaction solution, followed by separation. The aqueous layer was extracted with CH$_2$Cl$_2$ (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=100:1) to give the following compound (0.0576 g, 90%).

$R_f$ 0.69 (Hex:AcOEt=4:1); $^1$H NMR (400 MHz, CDCl$_3$) δ 7.29-7.20 (1H, m), 6.31 (1H, dd, J=15.4, 10.2 Hz), 6.11 (1H, dd, J=15.4, 11.0 Hz), 5.83-5.69 (2H, m), 5.34 (1H, q, J=6.3 Hz), 3.82-3.61 (5H, m), 2.78-2.62 (2H, m), 1.69-1.38 (15H, m), 1.39-1.00 (21H, m), 0.93 (3H, d, J=6.6 Hz).

[Chemical formula 51]

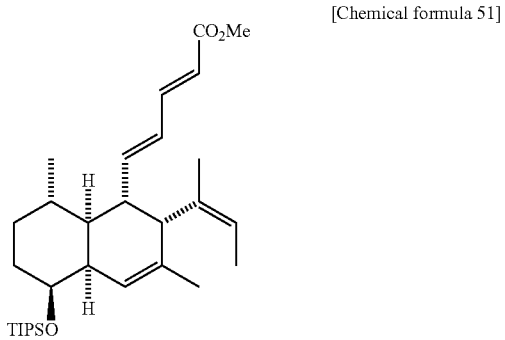

Production Step 4-(3)

A hexane solution (0.247 ml, 1.02 M) of DIBAL was added to a solution (2 ml) of the compound (0.0504 g, 0.101 mmol) obtained in production step 4-(2) in CH$_2$Cl$_2$ at −78° C. under an argon atmosphere, and the mixture was stirred. After the completion of the reaction, MeOH was added thereto until foams were no longer produced. The temperature of the solution was then raised to room temperature before a saturated aqueous potassium sodium tartarate solution (5 ml) was added thereto. The mixture was stirred for 30 min, followed by separation. The aqueous layer was extracted with CH$_2$Cl$_2$ (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=15:1) to give the following compound (0.0461 g, 99%).

$R_f$ 0.38 (Hex:AcOEt=4:1); $^1$H NMR (400 MHz, CDCl$_3$) δ 6.21 (1H, dd, J=15.1, 10.0 Hz), 5.99 (1H, dd, J=14.9, 10.0 Hz), 5.89 (1H, dd, J=14.9, 9.5 Hz), 5.77-5.68 (2H, m), 5.34 (1H, q, J=6.1 Hz), 4.17 (2H, dd, J=5.9, 5.9 Hz), 3.69 (1H, dt, J=11.0, 4.6 Hz), 2.71-2.57 (2H, m), 1.66-1.24 (16H, m), 1.11-1.01 (21H, m), 0.92 (3H, d, J=6.6 Hz).

[Chemical formula 52]

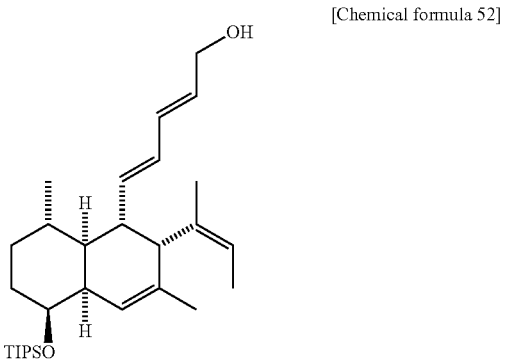

Production Step 4-(4)

2,6-Lutidine (0.134 ml, 1.15 mmol), a t-BuOH/30% H$_2$O$_2$ aq. (100/1) solution (0.294 ml, 0.039 M) of osmium tetroxide (OsO$_4$), and NaIO$_4$ (0.510 g, 2.38 mmol) were added in that order to a solution (4.8 ml) of the compound (0.136 g, 0.287 mmol) obtained in production step 4-(3) in dioxane/H$_2$O (3/1) under an argon atmosphere, and the mixture was stirred at room temperature for 2 hr. After the completion of the reaction, pure water (10 ml) was added to the reaction solution, followed by separation. The aqueous layer was extracted with Et$_2$O (10 ml×3), and the collected oil layer was dried over Na$_2$SO$_4$. The dried oil layer was filtered, and the solvent was then removed under the reduced pressure. The residue was purified by column chromatography on silica gel (Hex:AcOEt=80:1) to give the following compound (0.123 g, 96%).

$R_f$ 0.65 (Hex:AcOEt=4:1); $^1$H NMR (400 MHz, CDCl$_3$) δ 9.48 (1H, d, J=7.8 Hz), 7.02 (1H, dd, J=15.4, 10.7 Hz), 6.07 (1H, dd, J=15.4, 7.8 Hz), 5.79 (1H, s), 5.38 (1H, q, J=6.1 Hz), 3.78-3.69 (1H, m), 3.05-2.89 (1H, m), 2.69-2.60 (1H, m), 1.72-1.40 (16H, m), 1.10-1.01 (21H, m), 0.95 (3H, d, J=6.6 Hz).

[Chemical formula 53]

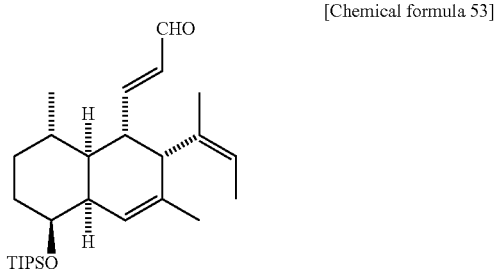

Production Step 4-(5)

A hexane solution (0.123 ml, 1.02 M) of DIBAL was added to a solution (2 ml) of the compound (0.0280 g, 0.0630 mmol) obtained in production step 4-(4) in CH$_2$Cl$_2$ at −78° C. under an argon atmosphere, and the mixture was stirred. After the completion of the reaction, MeOH was added thereto until foams were no longer produced. The temperature of the solution was then raised to room temperature before a saturated aqueous potassium sodium tartarate solution (5 ml) was added thereto. The mixture was stirred for 30 min, followed by separation. The aqueous layer was extracted with CH$_2$Cl$_2$ (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=15:1) to give the following compound (0.0280 g, quant.).

$R_f$ 0.44 (Hex:AcOEt=4:1); $^1$H NMR (400 MHz, CDCl$_3$) δ 5.87 (1H, dd, J=14.9, 9.8 Hz), 5.73 (1H, s), 5.58 (1H, dt, J=15.1, 6.1 Hz), 5.35 (1H, q, J=6.6 Hz), 4.07 (2H, dd, J=6.1, 6.1 Hz), 3.70 (1H, dt, J=11.0, 5.1 Hz), 2.72-2.56 (2H, m), 1.68-1.36 (16H, m), 1.13-1.01 (21H, m), 0.92 (3H, d, J=6.6 Hz).

[Chemical formula 54]

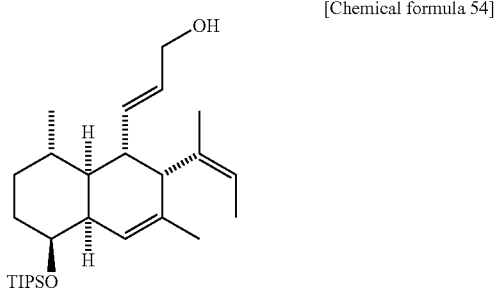

Production Step 4-(6)

Pyridine (0.0880 ml, 1.09 mmol), a t-BuOH/30% H$_2$O$_2$ aq. (100/1) solution (0.279 ml, 0.039 M) of OsO$_4$, and NaIO$_4$ (0.4657 g, 2.18 mmol) were added in that order to a solution (8.4 ml) of the compound (0.122 g, 0.272 mmol) obtained in production step 4-(5) in dioxane/H$_2$O (6/1) under an argon atmosphere, and the mixture was stirred at room temperature for 36 hr. After the completion of the reaction, the reaction solution as such was filtered by column chromatography on silica gel (Et$_2$O) to remove a white solid. After the filtration, the solvent was removed under the reduced pressure, and the residue was purified by column chromatography on silica gel (Hex:AcOEt=80:1) to give the following compound (0.0450 g, 39%).

R$_f$ 0.73 (Hex:AcOEt=4:1); $^1$H NMR (400 MHz, CDCl$_3$) δ 9.81 (1H, d, J=3.4 Hz), 5.81 (1H, s), 5.50 (1H, q, J=6.8 Hz), 3.78 (1H, dt, J=11.2, 4.4 Hz), 3.39-3.31 (1H, m), 2.76-2.66 (2H, m), 1.73-1.42 (15H, m), 1.10-1.01 (21H, m), 0.89 (3H, d, J=6.6 Hz).

[Chemical formula 55]

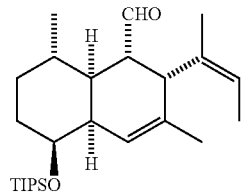

Production Step 4-(7)

NaBH$_4$ (0.0520 g, 1.37 mmol) was added to a solution (1.5 ml) of the compound (0.0381 g, 0.0910 mmol) obtained in production step 4-(6) in THF/MeOH (1/2) at 0° C. under an argon atmosphere, and the mixture was heated to room temperature and was stirred. After the completion of the reaction, a saturated aqueous NH$_4$Cl solution (3 ml) was added to the reaction solution, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=50:1) to give the following compound (0.0364 g, 95%).

R$_f$ 0.51 (Hex:AcOEt=4:1); $^1$H NMR (400 MHz, CDCl$_3$) δ 5.72 (1H, s), 5.48 (1H, q, J=5.9 Hz), 3.83-3.66 (2H, m), 3.58-3.42 (1H, m), 3.34-3.24 (1H, m), 2.64-2.46 (1H, m), 2.36-2.16 (1H, m), 1.77-1.34 (16H, m), 1.12-1.00 (21H, m), 0.91 (3H, d, J=3.9 Hz).

[Chemical formula 56]

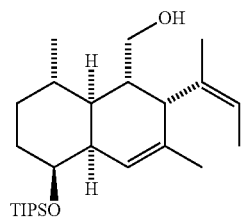

Production Step 4-(8)

OsO$_4$ (0.0300 g, 0.118 mmol) was added to a solution (0.5 ml) of the compound (0.0116 g, 0.0276 mmol) obtained in production step 4-(7) in pyridine under an argon atmosphere, and mixture was stirred for 30 min. After the completion of the reaction, a 20% aqueous NaHSO$_3$ solution (3 ml) was added to the reaction solution, and the mixture was stirred for about one hr, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=3:1) to give the following compound (0.0098 g, 78%).

R$_f$ 0.42 (Hex:AcOEt=1:1); $^1$H NMR (400 MHz, CDCl$_3$) δ 5.72 (1H, s), 4.03 (2H, dd, J=10.0, 7.8 Hz), 3.68-3.60 (1H, m), 3.52-3.46 (1H, m), 2.55-2.49 (1H, m), 2.48-2.42 (1H, m), 2.39-2.26 (2H, m), 1.78 (3H, s), 1.45 (3H, s), 1.33-1.17 (10H, m), 1.10-1.02 (21H, m), 0.88 (3H, d, J=6.1 Hz).

[Chemical formula 57]

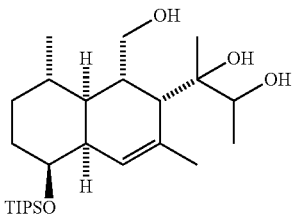

Production Step 4-(9)

[Ir(cod)pyr(PCy$_3$)]PF$_6$ (Crabtree's catalyst) (0.0018 g, 0.00224 mmol) was dissolved in degassed (CH$_2$Cl)$_2$ (0.4 ml) under an argon atmosphere. A solution of the compound (0.0045 g, 0.00990 mmol) obtained in production step 4-(8) dissolved in degassed (CH$_2$Cl)$_2$ (0.8 ml) was added to the solution. An H$_2$ gas (1 atm) was sealed. The temperature was then raised to 60° C., followed by stirring for 2 hr. After the completion of the reaction, a saturated aqueous NH$_4$Cl solution was added to the reaction solution, followed by separation. The aqueous layer was extracted with CH$_2$Cl$_2$, and the collected oil layer was dried over Na$_2$SO$_4$. The dried oil layer was filtered, and the solvent was then removed under the reduced pressure. The residue was purified by column chromatography on silica gel (Hex:AcOEt=3:1) to give the following compound (0.0039 g, 87%).

R$_f$ 0.39 (Hex:AcOEt=1:1); $^1$H NMR (400 MHz, CDCl$_3$) δ 4.15 (1H, dd, J=10.2, 8.0 Hz), 3.94-3.83 (1H, m), 3.69 (1H, dt, J=10.7, 5.4 Hz), 3.51-3.38 (1H, m), 2.51-2.40 (1H, m), 2.14-1.99 (1H, m), 1.78-1.60 (7H, m), 1.40 (3H, s), 1.29-1.15 (8H, m), 1.09-1.01 (21H, m), 0.99 (3H, d, J=5.1 Hz), 0.85 (3H, d, J=6.1 Hz).

[Chemical formula 58]

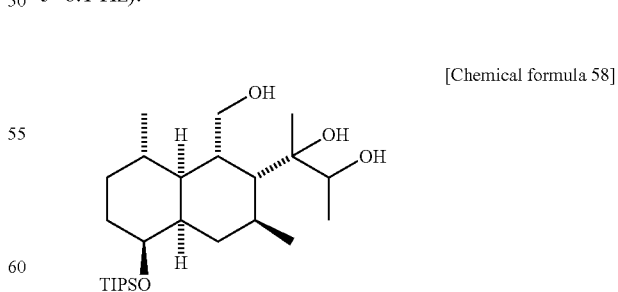

Production Step 4-(10)

Et$_3$N (0.0204 ml, 0.146 mmol) and BzCN (0.0153 g, 0.117 mmol) were added in that order to a solution (1 ml) of the compound (0.0084 g, 0.0184 mmol) obtained in production step 4-(9) in CH$_3$CN at −30° C. under an argon atmosphere, and the mixture was stirred for 10 min. After the completion of the reaction, a small amount of MeOH was added to the reaction solution. The temperature of the mixture was raised to room temperature, and the mixture was stirred for a while. The solvent was removed under the reduced pressure. The residue was purified by column chromatography on silica gel (Hex:AcOEt=5:1) to give the following compound (0.0083 g, 81%).

$R_f$ 0.31 (Hex:AcOEt=3:1); $^1$H NMR (400 MHz, CDCl$_3$) δ 8.09-8.00 (2H, m), 7.65-7.52 (1H, m), 7.51-7.41 (2H, m), 4.81 (1H, dd, J=11.0, 4.6 Hz), 4.38 (1H, dd, J=11.0, 8.6 Hz), 3.91-3.82 (1H, m), 3.74 (1H, dt, J=10.8, 5.1 Hz), 2.78-2.69 (1H, m), 2.18-2.09 (1H, m), 2.06-1.98 (1H, m), 1.82-1.58 (9H, m), 1.41 (3H, s), 1.24 (3H, d, J=6.0 Hz), 1.09-1.02 (21H, m), 1.00 (3H, d, J=6.0 Hz), 0.83 (3H, d, J=6.2 Hz).

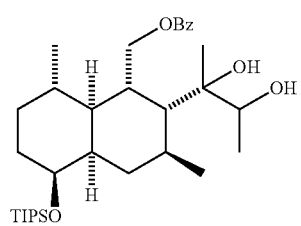

[Chemical formula 59]

Production Step 4-(11)

TCDI (0.0198 g, 0.110 mmol) and DMAP (0.0026 g, 0.0213 mmol) were added in that order to a solution (1 ml) of the compound (0.0118 g, 0.0210 mmol) obtained in production step 4-(10) in toluene under an argon atmosphere, and the mixture was stirred with heating under reflux for 17 hr. After the completion of the reaction, a saturated aqueous NH$_4$Cl solution (3 ml) was added to the reaction solution, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=15:1) to give the following compound (0.0087 g, 69%).

$R_f$ 0.60 (Hex:AcOEt=3:1); $^1$H NMR (400 MHz, CDCl$_3$) δ 8.13-8.07 (2H, m), 7.61-7.54 (1H, m), 7.50-7.42 (2H, m), 4.67 (1H, q, J=6.3 Hz), 4.59 (1H, dd, J=11.2, 7.3 Hz), 4.52 (1H, dd, J=11.2, 6.1 Hz), 3.71 (1H, dt, J=11.2, 4.6 Hz), 2.84-2.76 (1H, m), 2.17 (1H, dd, J=11.7, 3.9 Hz), 2.14-2.05 (1H, m), 1.89 (1H, dt, J=13.7, 3.9 Hz), 1.85-1.76 (1H, m), 1.76-1.59 (5H, m), 1.57 (3H, s), 1.54-1.50 (2H, m), 1.41 (3H, d, J=6.6 Hz), 1.04-0.97 (21H, m), 0.92 (3H, d, J=6.1 Hz), 0.91 (3H, d, J=5.9 Hz).

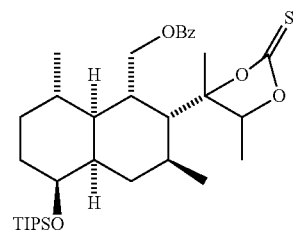

[Chemical formula 60]

Production step 4-(12)

A solution (0.5 ml) of the compound (0.0043 g, 0.00713 mmol) obtained in production step 4-(11) in P(OMe)$_3$ was stirred with heating under reflux under an argon atmosphere for 67 hr. After the completion of the reaction, the solvent was removed under the reduced pressure. The residue was purified by column chromatography on silica gel (Hex:AcOEt=80:1) to give the following compound (0.0037 g, 97%).

$R_f$ 0.78 (Hex:AcOEt=3:1); $^1$H NMR (400 MHz, CDCl$_3$) δ 8.03-7.97 (2H, m), 7.60-7.50 (1H, m), 7.48-7.39 (2H, m), 5.34 (1H, q, J=6.8 Hz), 4.46-4.30 (2H, m), 3.76-3.66 (1H, m), 2.58-2.46 (1H, m), 2.35-2.23 (2H, m), 2.15-1.97 (1H, m), 1.92-1.77 (3H, m), 1.71 (3H, s), 1.68-1.58 (8H, m), 1.10-0.96 (21H, m), 0.92 (3H, d, J=6.3 Hz), 0.86 (3H, d, J=6.1 Hz).

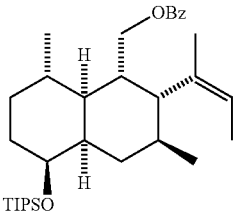

[Chemical formula 61]

Production Step 4-(13)

A hexane solution (0.0284 ml, 1.02 M) of DIBAL was added to a solution (1 ml) of the compound (0.0061 g, 0.0116 mmol) obtained in production step 4-(12) in CH$_2$Cl$_2$ at −78° C. under an argon atmosphere, and the mixture was stirred. After the completion of the reaction, MeOH was added thereto until foams were no longer produced. The temperature of the solution was then raised to room temperature before a saturated aqueous potassium sodium tartarate solution (5 ml) was added thereto. The mixture was stirred for 30 min, followed by separation. The aqueous layer was extracted with CH$_2$Cl$_2$ (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=20:1) to give the following compound (0.0041 g, 84%).

$R_f$ 0.71 (Hex:AcOEt=3:1).

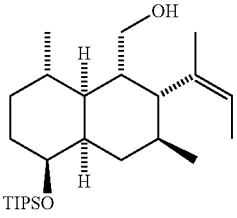

[Chemical formula 62]

Production Step 4-(14)

A Dess-Martin reagent (0.0160 g, 0.0377 mmol) was added to a solution (1 ml) of the compound (0.0041 g, 0.00970 mmol) obtained in production step 4-(13) in CH$_2$Cl$_2$ under an argon atmosphere, and the mixture was stirred at room temperature. After the completion of the reaction, the reaction solution was diluted with Et$_2$O (1 ml), and a saturated aqueous NaHCO$_3$ solution (2 ml) and a saturated aqueous Na$_2$S$_2$O$_3$ solution (2 ml) were added in that order to the diluted solution, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=100:1) to give the following compound (0.0034 g, 83%).

$R_f$ 0.49 (Hex:AcOEt=20:1); $^1$H NMR (400 MHz, CDCl$_3$) δ 10.0 (1H, d, J=2.7 Hz), 5.40 (1H, q, J=6.8 Hz), 3.76 (1H, dt, J=10.7, 4.9 Hz), 2.63-2.52 (2H, m), 2.18-2.08 (1H, m), 1.98-1.59 (15H, m), 1.10-0.99 (21H, m), 0.87 (3H, d, J=6.3 Hz), 0.87 (3H, d, J=6.1 Hz).

[Chemical formula 63]

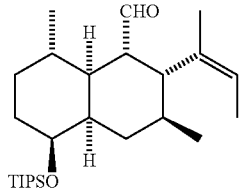

Production Step 4-(15)

A THF solution (0.0191 ml, 1.06 M) of LiHMDS was gradually added dropwise to a solution (0.3 ml) of phosphonate A (0.0127 g, 0.0508 mmol) in THF at −78° C. under an argon atmosphere, and the mixture was stirred for 30 min. A solution (0.9 ml) of the compound (0.0034 g, 0.00808 mmol) obtained in production step 4-(14) in THF was added to thereto, and the mixture was stirred for 2 hr. The mixture was then heated to 0° C. and stirred for one hr. After the completion of the reaction, a saturated aqueous NH$_4$Cl solution (3 ml) was added to the reaction solution, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=100:1) and was further purified by PTLC (Hex:benzene=1:1) to give the following compound (0.0024 g, 57%).

$R_f$ 0.44 (Hex:AcOEt=20:1); $^1$H NMR (400 MHz, CDCl$_3$) δ 7.32-7.21 (1H, m), 6.53 (1H, dd, J=14.6, 9.5 Hz), 6.08 (1H, dd, J=14.6, 11.0 Hz), 5.78 (1H, d, J=15.1 Hz), 5.26 (1H, q, J=6.3 Hz), 4.20 (2H, q, J=7.1 Hz), 3.72-3.64 (1H, m), 2.53-2.43 (2H, m), 2.17-2.07 (1H, m), 1.94-1.78 (2H, m), 1.76-1.46 (13H, m), 1.29 (3H, t, J=7.1 Hz), 1.08-1.00 (21H, m), 0.91 (3H, d, J=6.3 Hz), 0.81 (3H, d, J=6.3 Hz).

[Chemical formula 64]

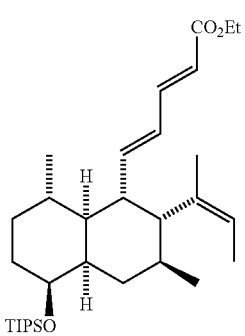

Production Step 4-(16)

LiOH.H$_2$O (0.0252 g, 0.600 mmol) was added to a solution (0.75 ml) of the compound (0.0031 g, 0.00600 mmol) obtained in production step 4-(15) in EtOH/H$_2$O (4/1) under an argon atmosphere, and the mixture was stirred at room temperature for 43 hr. After the completion of the reaction, a saturated aqueous NH$_4$Cl solution (3 ml) was added to the reaction solution, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=4:1) to give the following compound (0.0029 g, quant.).

$R_f$ 0.73 (Hex:AcOEt=1:1); $^1$H NMR (400 MHz, CDCl$_3$) δ 7.35 (1H, dd, J=15.4, 11.2 Hz), 6.59 (1H, dd, J=15.4, 10.0 Hz), 6.12 (1H, dd, J=15.4, 11.2 Hz), 5.79 (1H, d, J=15.4 Hz), 5.26 (1H, q, J=7.1 Hz), 3.73-3.65 (1H, m), 2.55-2.43 (2H, m), 2.16-2.07 (1H, m), 1.93-1.78 (2H, m), 1.75-1.46 (13H, m), 1.12-0.97 (21H, m), 0.91 (3H, d, J=6.3 Hz), 0.82 (3H, d, J=6.3 Hz).

[Chemical formula 65]

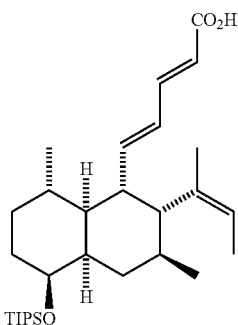

Production Step 4-(17)

A THF solution (0.0634 ml, 1.0 M) of TBAF was added to a solution (0.5 ml) of the compound (0.0031 g, 0.00634 mmol) obtained in production step 4-(16) in THF under an argon atmosphere, and the mixture was stirred at room temperature for 76 hr. After the completion of the reaction, an aqueous 1N-HCl solution (3 ml) was added to the reaction solution, followed by separation. The aqueous layer was extracted with Et$_2$O (5 ml×3), and the collected oil layer was dried over Na$_2$SO$_4$. The dried oil layer was filtered, and the solvent was then removed under the reduced pressure. The residue was purified by column chromatography on silica gel (Hex:AcOEt=3:2) to give the title compound (0.0015 g, 71%).

$R_f$ 0.29 (Hex:AcOEt=1:1); $^1$H NMR (400 MHz, CDCl$_3$) 7.35 (1H, dd, J=15.4, 11.0 Hz), 6.63 (1H, dd, J=14.9, 9.8 Hz), 6.13 (1H, dd, J=14.9, 11.0 Hz), 5.79 (1H, d, J=15.4 Hz), 5.27 (1H, qd, J=6.8, 1.0 Hz), 3.67 (1H, ddd, J=11.5, 4.9, 4.9 Hz), 2.58-2.46 (2H, m), 2.24-2.14 (1H, m), 1.93-1.62 (7H, m), 1.59 (3H, dd, J=6.8, 0.7 Hz), 1.51 (3H, s), 1.24-1.00 (2H, m), 0.94 (3H, d, J=6.3 Hz), 0.83 (3H, d, J=6.1 Hz); FAB-MS: [M+Na]$^+$ calculated for C$_{21}$H$_{32}$O$_3$Na: 355.2249. Found: 355.2249.

[Chemical formula 66]

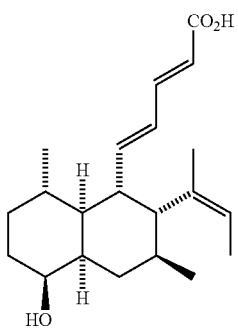

Test Example 1

Evaluation of Control Effect (1) Preparation of Test Solutions

The compounds obtained in Examples 1 to 3 were dissolved in acetone to bring the concentration of the compounds to 1 mg/mL. Ten-fold diluted Neoesterin (manufactured by KUMIAI CHEMICAL INDUSTRY CO., LTD.) (1 μL) was added to 20 μL of the solutions. Further, 180 μL of deionized water was added thereto to regulate the concentration to 100 ppm to prepare test solutions.

(2) Measurement of Control Effect

The control effect was measured by measuring the preventive value of each of the test solutions. The preventive value was calculated by the following method.

At the outset, leaves cut by a leaf punch off from the leaves at the third and fourth stages of cabbage were allowed to stand still on a multi-well plate. An appropriate amount of the test solution was sprayed followed by air drying.

Next, a spore suspension ($2.0 \times 10^5$ cells/mL) of *Botrytis cinerea* was prepared as an inoculating microorganism liquor and was inoculated by spraying in an amount of 20 mL per 7 to 10 multi-well plate. Infection with *Botrytis cinerea* was carried out in a light shielding chamber (temperature 21° C., humidity about 100%), and the preventive value was calculated three days after the infection.

The intensity of pathogenesis was determined in four grades of 0 (zero) to three according to the following criteria, and the preventive value was calculated using the following equations.

0; No pathogenesis was found.
1; Slight pathogenesis was found.
2; Control effect was found as compared with untreated plot, although diseases were developed.
3; Phathogenesis equivalent to that in untreated plot was found.

$$\text{Severity} = \frac{\text{Average intensity of pathogenesis } (n=4) \times 100}{3} \quad \text{[Numeral formula 1]}$$

$$\text{Preventive value} = \frac{\left(\begin{array}{l}\text{Severity in untreated plot} - \\ \text{severity in treated plot}\end{array}\right) \times 100}{\text{Severity in untreated plot}} \quad \text{[Numeral formula 2]}$$

As a result, it was confirmed that all the test compounds had a preventive value equivalent to that of MK8383, indicating that the test compounds had a control effect equivalent to that of MK8383.

TABLE 3

| Compound name | Preventive value |
| --- | --- |
| Compound of Example 1 | 92 |
| Compound of Example 2 | 100 |
| Compound of Example 3 | 100 |
| MK8383 | 100 |

Test Example 2

Evaluation of Photostability (1) Preparation of Test Solutions

The compounds obtained in Examples 1 to 3 were dissolved in acetone, and the concentration of the compounds was adjusted to 200 μg/mL (100 μg/mL for the compound of Example 3) to give test solutions.

(2) Measurement of Photostability

The photostability was determined by measuring the residual ratio of compound after exposure to light. The residual ratio was calculated by the following method.

The test solution (500 μL) was dispensed in a glass Petri dish having a diameter of 5 cm, and the solvent was removed by evaporation under light shielding conditions to form a dry film. The dry film was exposed to a sunlight lamp within a chamber (temperature 25° C., humidity 60%) and was recovered 24 hr after the start of the exposure. The exposed film was washed with 500 μL of methanol and was analyzed by HPLC (manufactured by Nihon Waters K.K.). The residual ratio (concentration ratio after the elapse of each hour when the residual ratio at 0 hr was presumed to be 100%) was calculated by regarding the peak area as the concentration of the compound. The light used in the exposure had an illuminance of 30,000 lux and an ultraviolet intensity of 300 to 400 μW/cm².

As a result, it was confirmed that all the test compounds had a higher residual ratio than MK8383, indicating that the test compounds had high photostability.

TABLE 4

| Compound name | Residual ratio after 24 hr |
| --- | --- |
| Compound of Example 1 | 100 |
| Compound of Example 2 | 108 |
| Compound of Example 3 | 95 |
| MK8383 | 14 |

Test Example 3

Antimicrobial Activity Test (1) Preparation of Test Solution

The compound of Example 3 was dissolved in DMSO, and the solution was adjusted to a concentration of 1.25 mg/mL to give a test solution.

(2) Measurement of Antimicrobial Activity

The antimicrobial activity was measured by using the extension of hypha as an index.

Individual plant pathogenic fungi were cultured with shaking using a potato sucrose broth (PSB) at 21 to 25° C. under fully darkened conditions for 5 days. The cultured suspension was ground with Hiscotoron and was 100-fold diluted with fresh PSB to give a test suspension.

The test suspension (100 μL) and the test solution (1 μL) were mixed together in a 96-hole plate (final concentration: 12.5 ppm), and the mixture was cultured at 21 to 25° C. for 3 days.

The extension of hypha was determined according to the following criteria.

+++; Extension of hypha was not found.
++; Extension of hypha was slightly found.
+; Inhibition of extension of hypha was found as compared with the extension of hypha of the control, although the extension of hypha was found.
−; Inhibition of extension of hypha was not found.

As a result, it was demonstrated that the compound of Example 3 had antimicrobial activity against various fungi.

TABLE 5

| Test fungi | Inhibition of extension |
| --- | --- |
| *Botrytis cinerea* | +++ |
| *Alternaria kikutiana* | ++ |

TABLE 5-continued

| Test fungi | Inhibition of extension |
|---|---|
| Cercospora beticola | +++ |
| Colletotrichum lagenarium | ++ |
| Pyricularia oryzae | ++ |
| Rhizoctonia solani | +++ |
| Leptosphaeria nodorum | ++ |

The invention claimed is:

1. A compound represented by formula (I) or its agriculturally and horticulturally acceptable salt:

[Chemical formula 1]

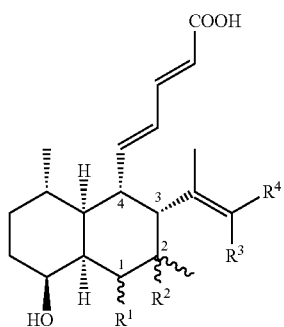

(I)

wherein
- $R^1$ and $R^2$ are hydrogen atoms, or $R^1$ and $R^2$ together combine with the carbon atom to which they are attached to form a cyclopropane ring,
- $R^3$ and $R^4$, which may be the same or different, are a hydrogen atom or $C_{1-6}$ alkyl, and
- a wavy line indicates that $R^1$, $R^2$, and methyl at the 2-position are independently in an alpha configuration or a beta configuration.

2. The compound or its agriculturally and horticulturally acceptable salt according to claim 1, wherein, when one of $R^3$ and $R^4$ is a hydrogen atom, the other is $C_{1-6}$ alkyl.

3. The compound or its agriculturally and horticulturally acceptable salt according to claim 1, wherein, when one of $R^3$ and $R^4$ is a hydrogen atom, the other is $C_{1-4}$ alkyl.

4. The compound or its agriculturally and horticulturally acceptable salt according to claim 1, wherein, when one of $R^3$ and $R^4$ is a hydrogen atom, the other is $C_{1-2}$ alkyl.

5. The compound or its agriculturally and horticulturally acceptable salt according to claim 1, wherein $R^1$ and $R^2$ are in an alpha configuration and methyl at the 2-position is in a beta configuration.

6. The compound or its agriculturally and horticulturally acceptable salt according to claim 1, wherein $R^1$ and $R^2$ are hydrogen atoms; when one of $R^3$ and $R^4$ is a hydrogen atom, the other is $C_{1-4}$ alkyl; $R^1$ and $R^2$ are in an alpha configuration; and methyl at the 2-position is in a beta configuration.

7. The compound or its agriculturally and horticulturally acceptable salt according to claim 1, wherein $R^1$ and $R^2$ are hydrogen atoms; when one of $R^3$ and $R^4$ is a hydrogen atom, the other is $C_{1-2}$ alkyl; $R^1$ and $R^2$ are in an alpha configuration; and methyl at the 2-position is in a beta configuration.

8. The compound or its agriculturally and horticulturally acceptable salt according to claim 1, wherein $R^1$ and $R^2$ together combine with the carbon atom to which they are attached to form a cyclopropane ring; when one of $R^3$ and $R^4$ is a hydrogen atom, the other is $C_{1-4}$ alkyl; $R^1$ and $R^2$ are in an alpha configuration; and methyl at the 2-position is in a beta configuration.

9. The compound or its agriculturally and horticulturally acceptable salt according to claim 1, wherein $R^1$ and $R^2$ together combine with the carbon atom to which they are attached to form a cyclopropane ring; when one of $R^3$ and $R^4$ is a hydrogen atom, the other is $C_{1-2}$ alkyl; $R^1$ and $R^2$ are in an alpha configuration; and methyl at the 2-position is in a beta configuration.

10. The compound or its agriculturally and horticulturally acceptable salt according to claim 1, wherein the compound of formula (I) is selected from the group consisting of
- (2E,4E)-5-{(1S,4S,4aS,5S,6R,7S,8aR)-6-[(Z)-but-2-en-2-yl]-decahydro-1-hydroxy-4,7-dimethylnaphthalen-5-yl}penta-2,4-dienoic acid;
- (2E,4E)-5-{(1S,4S,4aS,5S,6R,7S,8aR)-6-[(E)-but-2-en-2-yl]-decahydro-1-hydroxy-4,7-dimethylnaphthalen-5-yl}penta-2,4-dienoic acid; and
- (2E,4E)-5-{(1aR,2R,3S,3aS,4S,7S,7aS,7bR)-2-[(E)-but-2-en-2-yl]-decahydro-7-hydroxy-1a,4-dimethyl-1H-cyclopropa[a]naphthalen-3-yl}penta-2,4-dienoic acid.

11. An agricultural and horticultural disease control composition, comprising a compound or its agriculturally and horticulturally acceptable salt according to claim 1 as an active ingredient together with a solid carrier, liquid carrier, gaseous carrier, surfactant, dispersant or other adjuvant.

12. The agricultural and horticultural disease control agent according to claim 11, which is an agricultural and horticultural fungicide.

13. A method for controlling plant pathogenic microorganisms, comprising applying an effective amount of a compound or its agriculturally and horticulturally acceptable salt according to claim 1, to plant, seed, or soil.

14. The method according to claim 13, wherein the plant pathogenic microorganisms are plant pathogenic fungi.

15. A method for the manufacture of an agricultural and horticultural disease control agent, which comprises mixing the compound or its agriculturally and horticulturally acceptable salt according to claim 1 together with a solid carrier, liquid carrier, gaseous carrier, surfactant, dispersant or other adjuvant.

16. The method according to claim 15, wherein the agricultural and horticultural disease control agent is an agricultural and horticultural fungicide.

* * * * *